(12) United States Patent
Ichikawa et al.

(10) Patent No.: US 8,926,609 B2
(45) Date of Patent: Jan. 6, 2015

(54) TREATMENT DEVICE AND TREATMENT METHOD

(71) Applicant: Olympus Medical Systems Corp., Tokyo (JP)

(72) Inventors: Hiroaki Ichikawa, Yokohama (JP); Hideyuki Kasahara, Hamura (JP); Hiroshi Kakidachi, Hino (JP); Masato Tamai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 234 days.

(21) Appl. No.: 13/668,930

(22) Filed: Nov. 5, 2012

(65) Prior Publication Data

US 2013/0172885 A1    Jul. 4, 2013

Related U.S. Application Data

(60) Provisional application No. 61/556,995, filed on Nov. 8, 2011.

(51) Int. Cl.
| | |
|---|---|
| *A61B 18/18* | (2006.01) |
| *A61B 18/08* | (2006.01) |
| *A61B 18/14* | (2006.01) |
| *A61B 18/00* | (2006.01) |

(52) U.S. Cl.
CPC ..... *A61B 18/1445* (2013.01); *A61B 2018/1455* (2013.01); *A61B 2018/00619* (2013.01); *A61B 18/085* (2013.01)
USPC ............................................................. 606/51

(58) Field of Classification Search
USPC ............................................................. 606/51
See application file for complete search history.

(56) References Cited

U.S. PATENT DOCUMENTS

| | | | |
|---|---|---|---|
| 2009/0248002 | A1 | 10/2009 | Takashino et al. |
| 2013/0131651 | A1* | 5/2013 | Strobl et al. ............... 606/1 |

* cited by examiner

*Primary Examiner* — Robert N Wieland
(74) *Attorney, Agent, or Firm* — Oliff PLC

(57) ABSTRACT

A surgical device which is configured to apply energy to living tissue and to be used to perform a surgical procedure includes a grasping portion, an incising portion, an introduction portion and a treatment portion. The grasping portion grasps the living tissue having a first surface and a second surface. The incising portion is movable forward and backward with respect to the living tissue and incises the living tissue. The introduction portion is movable forward and backward with respect to the living tissue and introduces a biocompatible material, which is chemically bound with the living tissue, to a space between the first surface and the second surface. The treatment portion is configured to apply high-frequency energy and thermal energy to the living tissue.

10 Claims, 19 Drawing Sheets

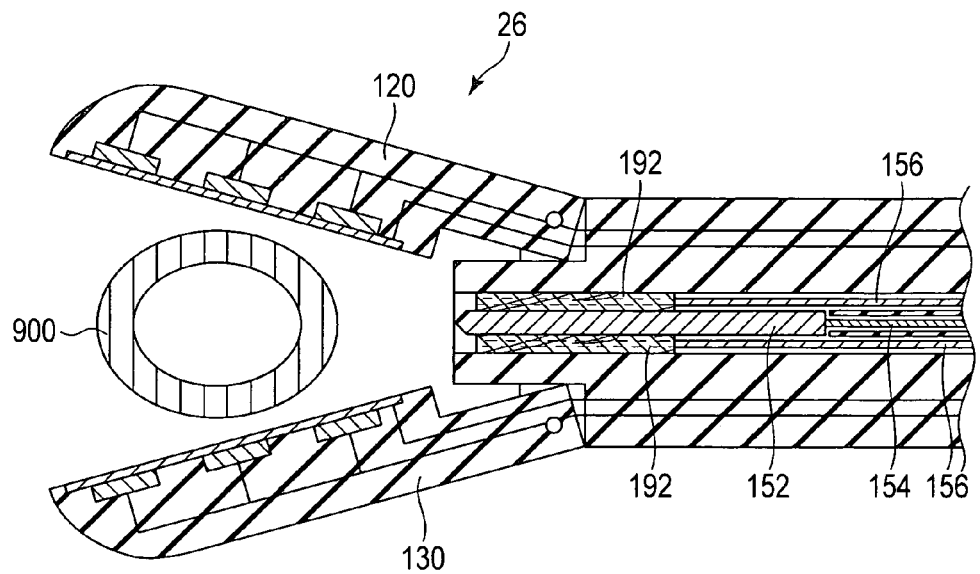
F I G. 3A
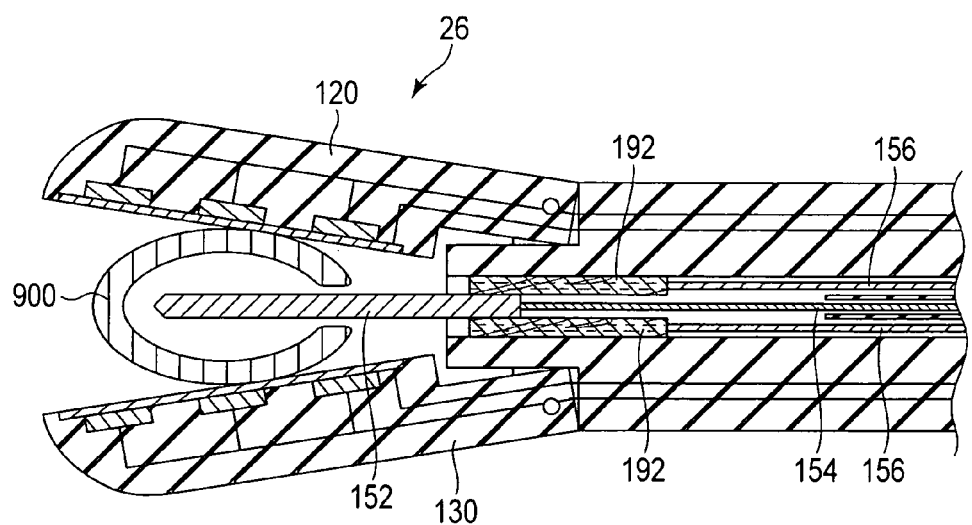
F I G. 3B

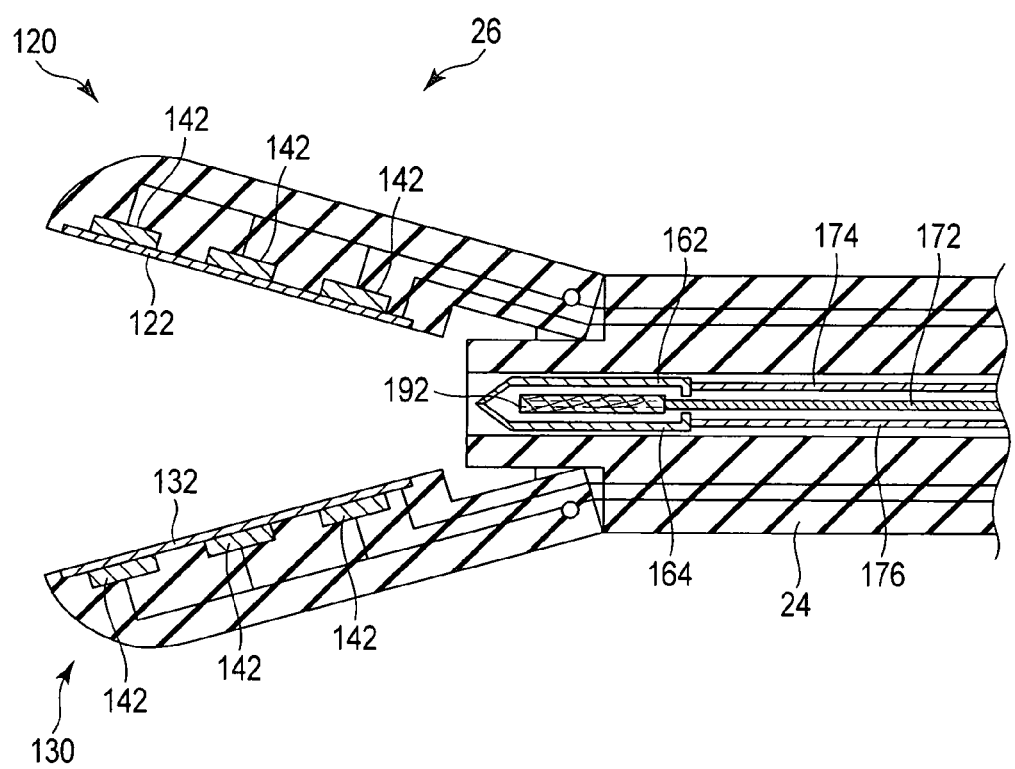
F I G. 4

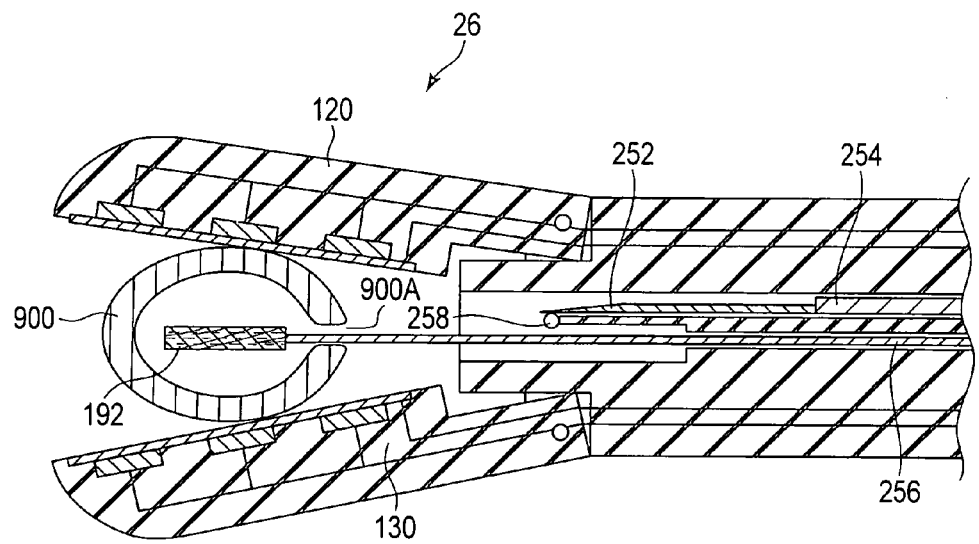
F I G. 7C
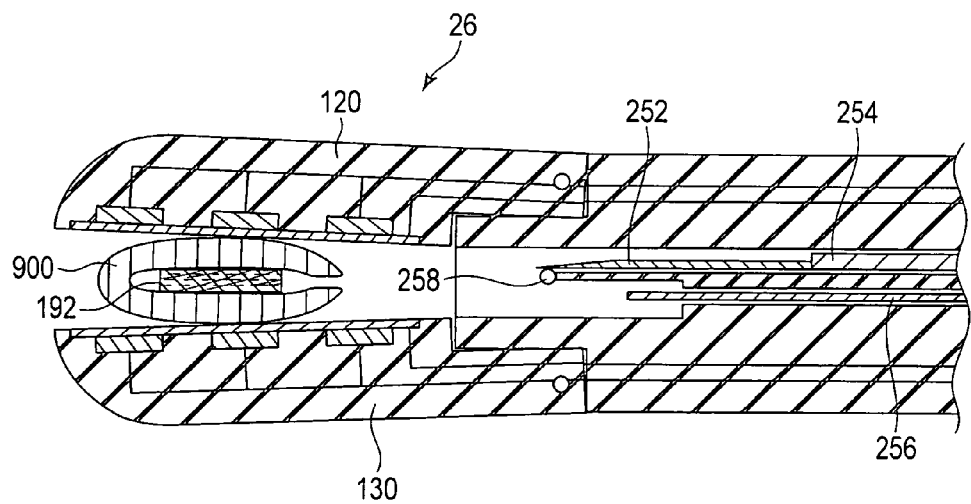
F I G. 7D

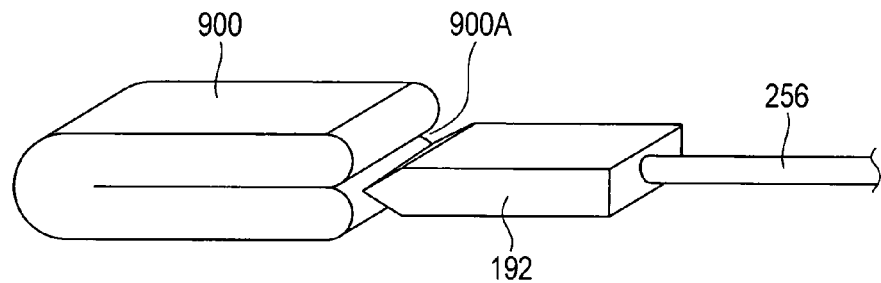
F I G. 8
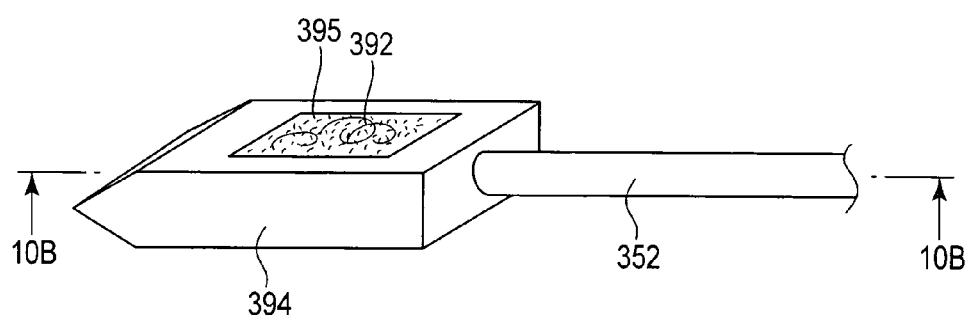
F I G. 10A
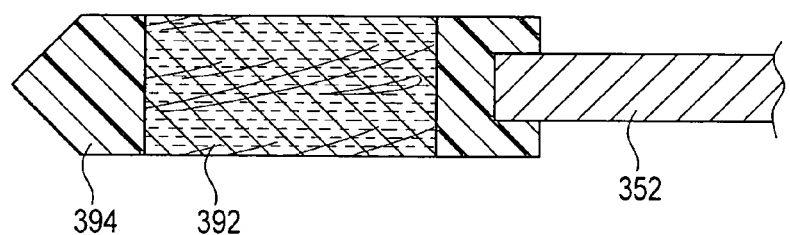
F I G. 10B

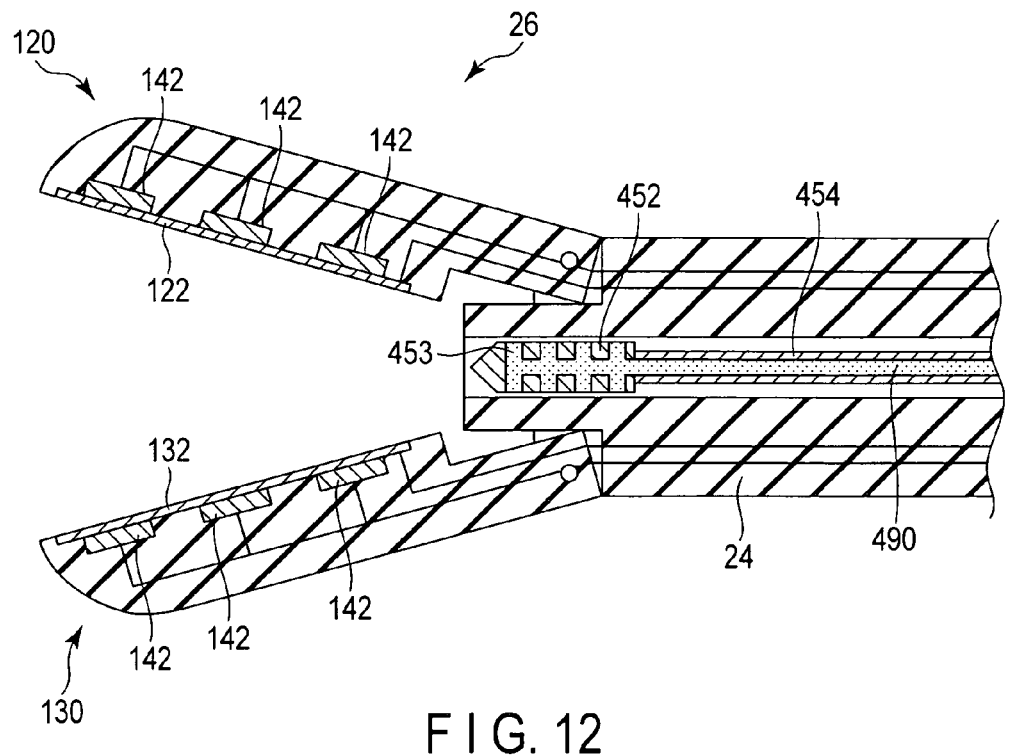
F I G. 12
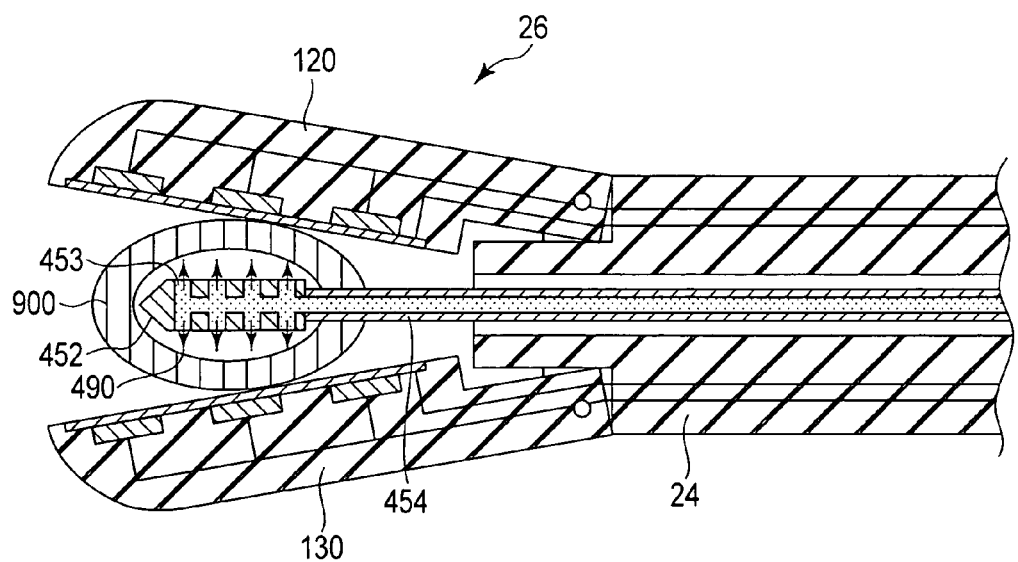
F I G. 13

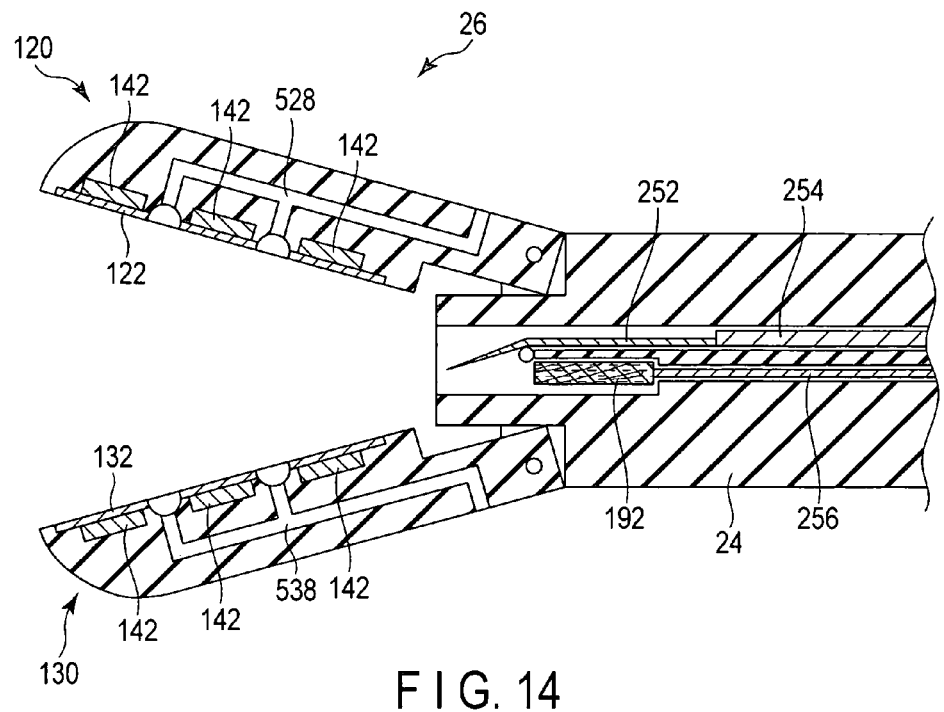
F I G. 14
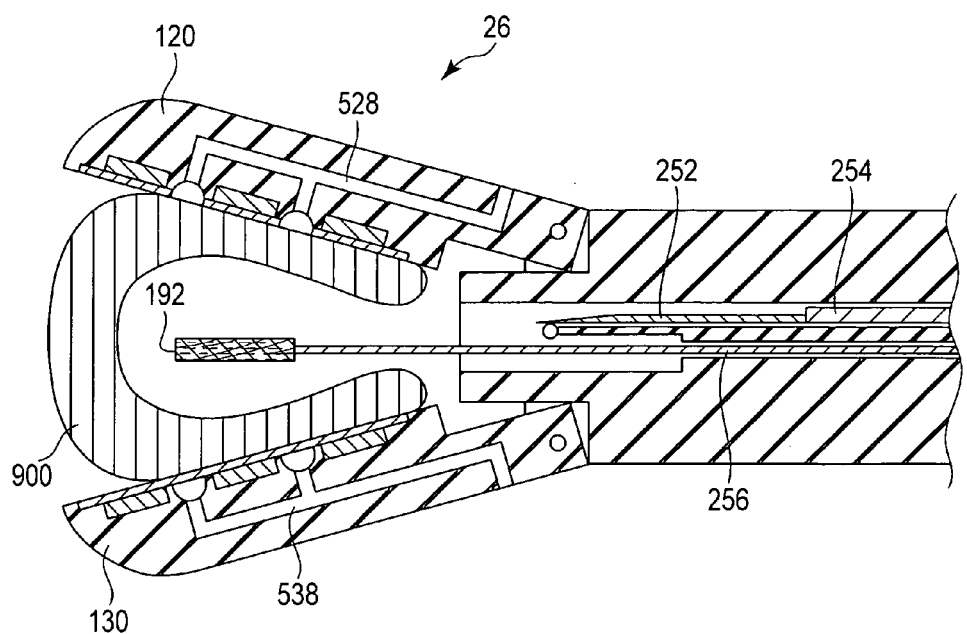
F I G. 15

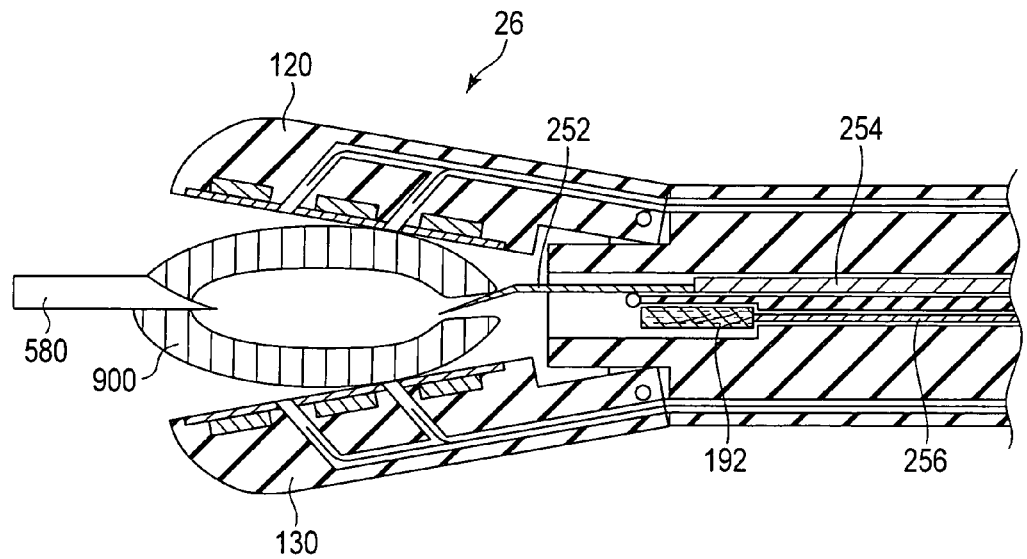
F I G. 18
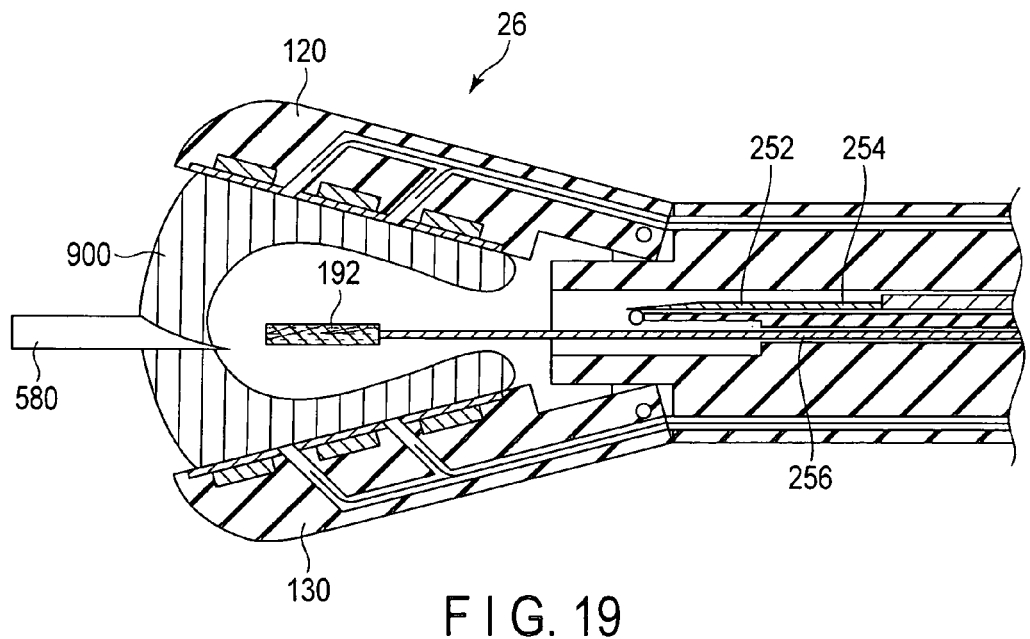
F I G. 19

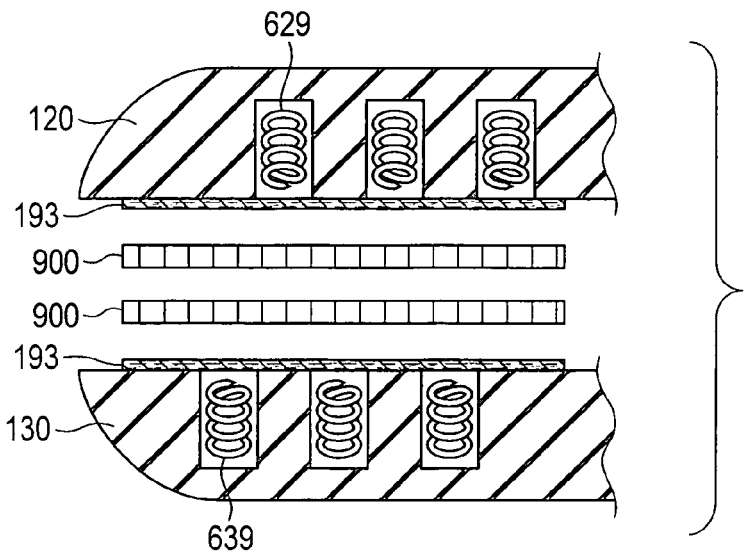
F I G. 22A
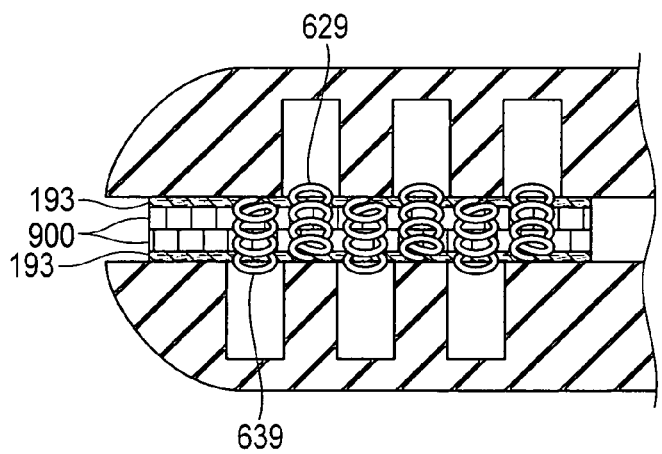
F I G. 22B
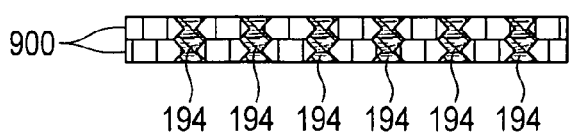
F I G. 22C

TREATMENT DEVICE AND TREATMENT METHOD

CROSS REFERENCE TO RELATED APPLICATIONS

This application claims the benefit of U.S. Provisional Application No. 61/556,995, filed Nov. 8, 2011, the entire contents of which are incorporated herein by reference.

BACKGROUND OF THE INVENTION

1. Field of the Invention

The present invention relates to a treatment device and a treatment method.

2. Description of the Related Art

In general, an energized surgical device used to perform surgery on living tissue by using high-frequency energy or thermal energy is known. For example, US2009/0248002A1 discloses the following energized surgical device. This surgical device has an openable and closable grasping portion that grasps living tissue which constitutes an intervention site. A high-frequency electrode configured to apply a high-frequency voltage is provided on a portion of this grasping portion that comes into contact with the living tissue. Further, a heater member configured to heat the living tissue through this high-frequency electrode is arranged on the high-frequency electrode. Furthermore, a holding portion comprises a cutter. In use of such a surgical device, first, the living tissue is grasped by the grasping portion, a high-frequency voltage is applied, and the living tissue is heated. Moreover, the living tissue is heated by using the heater member. The surgical device welds the living tissue based on these heating steps. Additionally, a living tissue end portion, which is in the welded state, can be cut by using a cutter provided to the grasping portion.

BRIEF SUMMARY OF THE INVENTION

According to an aspect of the present invention, a surgical device which applies energy to living tissue and is used to perform a surgical procedure includes a grasping portion which is configured to grasp the living tissue having a first surface and a second surface facing the first surface; an incising portion which is movable forward and backward with respect to the living tissue grasped by the grasping portion and is configured to incise the living tissue; an introduction portion which is movable forward and backward with respect to the living tissue and is configured to introduce a biocompatible material, which is chemically bound with the living tissue by application of high-frequency energy, to a space between the first surface and the second surface of the incised living tissue; and a treatment portion which is configured to apply the high-frequency energy to the living tissue to chemically bind the biocompatible material with the living tissue, is also configured to apply thermal energy to the living tissue to weld the first surface and the second surface, and is provided on the grasping portion.

According to an aspect of the present invention, an energized surgical method includes grasping living tissue having a first surface and a second surface facing the first surface by using a treatment portion; introducing a biocompatible material, which chemically binds with the living tissue, into a space between the first surface and the second surface; applying high-frequency energy to a portion where the first surface and the second surface of the living tissue face each other by using an electrode to weld the first surface and the second surface; and applying thermal energy to the portion where the first surface and the second surface of the living tissue face each other to weld the first surface and the second surface.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3A is a first schematic view for explaining a surgical procedure using the surgical device according to the first embodiment;

FIG. 3B is a second schematic view for explaining the surgical procedure using the surgical device according to the first embodiment;

FIG. 4 is a view showing a structural example of an end portion of the surgical device according to a modification of the first embodiment;

FIG. 7C is a third schematic view for explaining the surgical procedure using the surgical device according to the second embodiment;

FIG. 7D is a fourth schematic view for explaining the surgical procedure using the surgical device according to the second embodiment;

FIG. 8 is a view for explaining an example of a preferred shape of an artificial collagen sheet according to a second embodiment;

FIG. 10A is a perspective view showing a structural example of a casing according to the third embodiment;

FIG. 10B is a cross-sectional view showing a structural example of the casing according to the third embodiment;

FIG. 12 is a view showing a structural example of an end portion of the surgical device according to a fourth embodiment;

FIG. 13 is a schematic view for explaining a surgical procedure using the surgical device according to the fourth embodiment;

FIG. 14 is a view showing a structural example of an end portion of the surgical device according to a fifth embodiment;

FIG. 15 is a schematic view for explaining a surgical procedure using the surgical device according to the fifth embodiment;

FIG. 18 is a view showing a structural example of an end portion of the surgical device according to a second modification of the fifth embodiment;

FIG. 19 is a schematic view for explaining a surgical procedure using the surgical device according to the second modification of the fifth embodiment;

FIG. 22A is a first schematic view for explaining a surgical procedure using the surgical device according to a modification of the sixth embodiment;

FIG. 22B is a second schematic view for explaining the surgical procedure using the surgical device according to the modification of the sixth embodiment; and FIG. 22C is a third schematic view for explaining the surgical procedure using the surgical device according to the modification of the sixth embodiment.

DETAILED DESCRIPTION OF THE INVENTION

First Embodiment

Figure 1:
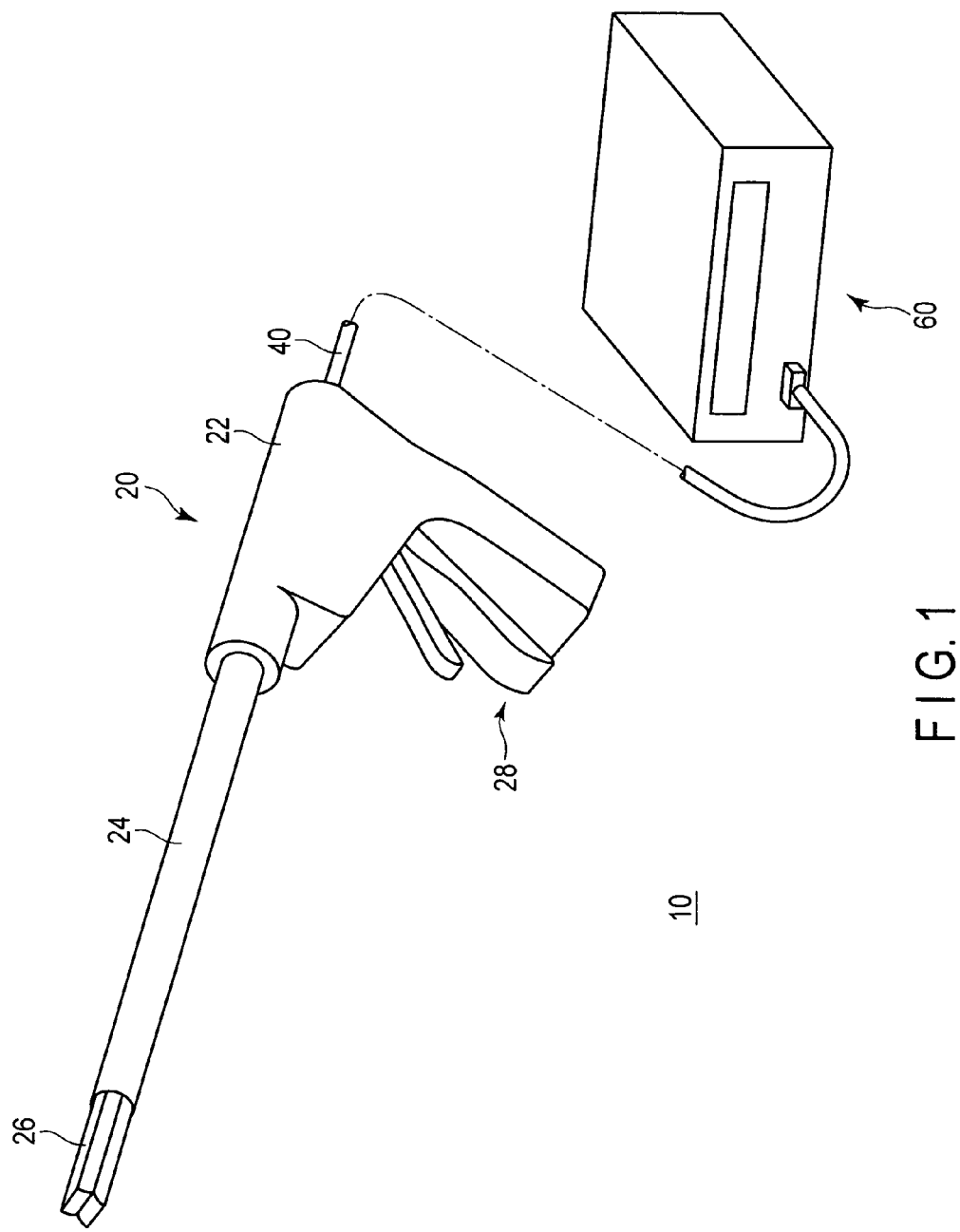
FIG. 1 is a schematic view showing a structural example of an energized surgical system according to each embodiment of the present invention.

A first embodiment according to the present invention will now be described with reference to FIG. 1 to FIG. 3D. An energized surgical system 10 according to this embodiment is used for surgery on living tissue. The surgical system 10 allows high-frequency energy and thermal energy to act on living tissue constituting an intervention site and is used to perform a surgical procedure on the living tissue. As shown in FIG. 1, the surgical system 10 has a surgical device 20 and a control apparatus 60.

The surgical device 20 is, for example, a linear surgical device configured to penetrate an abdominal wall and be used to perform a surgical procedure. The surgical device 20 includes a handle 22, a shaft 24 disposed on the handle 22, and a grasping portion 26 provided at the end of the shaft 24. The grasping portion 26 is a treatment portion which is openable and closable, grasps living tissue which constitutes an intervention site, and is used to perform a surgical procedure, for example, incision or welding of the living tissue. For the illustrative purpose, the grasping portion 26 side will be referred to as a distal end side and the handle 22 side will be referred to as a proximal end side hereinafter. The handle 22 comprises operation knobs 28 configured to operate the grasping portion 26. Any number of operation knobs 28 may be provided, and the number of operation knobs 28 required for manipulations are provided on the handle 22 in accordance with operations of the surgical device 20. It is to be noted that a shape of the surgical device 20 described herein is just an example as a matter of course, and any other shape can be adopted as long as the surgical device 20 has the same functions. For example, the shaft 24 may be bent, or the operation knob 28 formed into a finger grip shape or any other shape may be included.

The handle 22 is connected to the control apparatus 60 through a cable 40. The control apparatus 60 has a power supply for energy that is supplied to the surgical device 20, a drive circuit which drives each portion in the later-described surgical device 20, a control portion that controls operations of this drive circuit, and others. The control apparatus 60 controls energy that is supplied to the surgical device 20 and thereby controls application of a high-frequency voltage to living tissue or heating which will be described later in detail.

Figure 2:
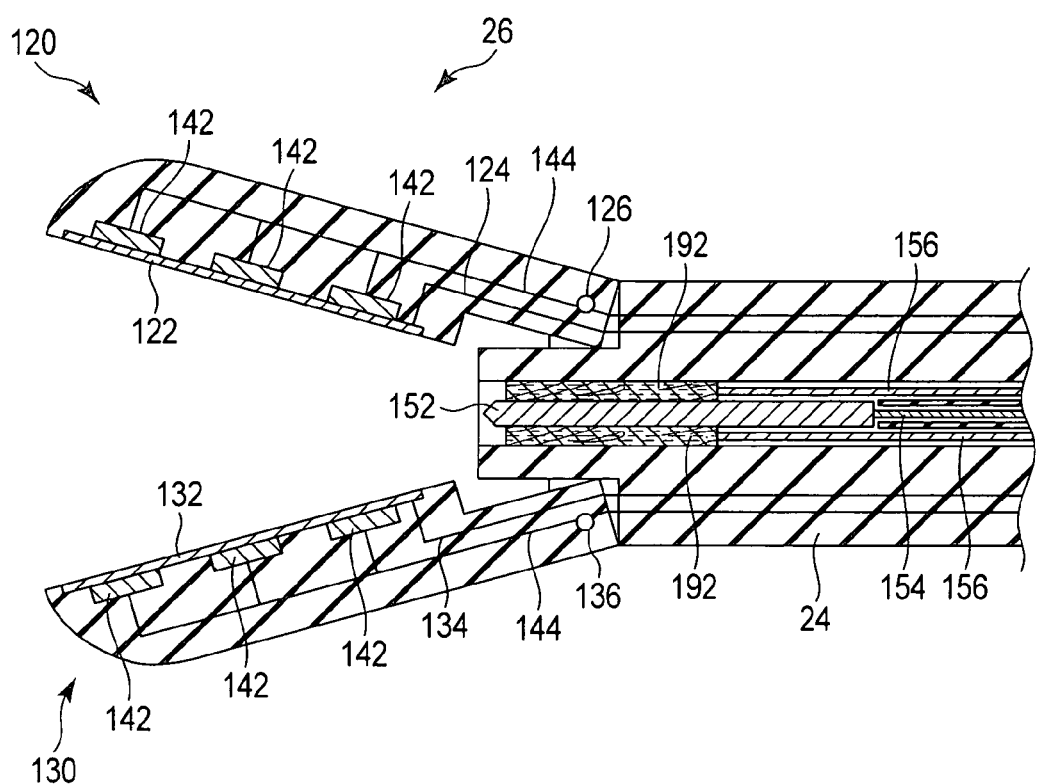
FIG. 2 is a view showing a structural example of an end portion of the surgical device according to a first embodiment.

FIG. 2 shows an example of a surrounding configuration of the grasping portion 26 and the shaft 24 on the distal end side. The grasping portion 26 has a first holding member 120 and a second holding member 130. The first holding member 120 rotates about a first rotary shaft 126 provided in a connecting portion for the shaft 24. Additionally, the second holding member 130 rotates about a second rotary shaft 136 provided in a connecting portion for the shaft 24. As a result, the grasping portion 26 comprising the first holding member 120 and the second holding member 130 opens and closes. This opening/closing operation is performed when a user operates one of the operation knobs 28. The grasping portion 26, which opens or closes, grasps or releases living tissue constituting an intervention site. When the grasping portion 26 is closed, the grasping portion 26 and the shaft 24 have a substantially cylindrical shape as a whole.

The first holding member 120 and the second holding member 130 are driven by, for example, pulling a wire. For example, the first holding member 120 or the second holding member 130 is connected to one of the operation knobs 28 through a wire. The grasping portion 26 is configured to be opened or closed by pulling or loosening this wire. Here, a spring may be provided near each of the first rotary shaft 126 and the second rotary shaft 136 so that biasing force can be given to the first holding member 120 and the second holding member 130. Furthermore, the wire does not have to be used. For example, a spring that gives the biasing force is provided near each of the first rotary shaft 126 and the second rotary shaft 136 so that each of the first holding member 120 and the second holding member 130 can be opened. Moreover, a slidable cylindrical body coupled with one of the operation knob 28 is provided to the shaft 24. As a configuration of the grasping portion 26, the first holding member 120 and the second holding member 130 may be closed against the biasing force of the spring when the first holding member 120 and the second holding member 130 are covered with the cylindrical body, and these holding members 120 and 130 may be opened by the biasing force of the spring when the first holding member 120 and the second holding member 130 are not covered with the cylindrical body.

A first high-frequency electrode 122 is provided on a surface of the first holding member 120 that comes into contact with living tissue which constitutes an intervention site. Likewise, a second high-frequency electrode 132 is provided on a surface of the second holding member 130 that comes into contact with the living tissue which constitutes an intervention site. The first high-frequency electrode 122 and the second high-frequency electrode 132 are provided to face each other in a state that the grasping portion 26 is closed. Each of the first high-frequency electrode 122 and the second high-frequency electrode 132 is made of a material having excellent electrical conductive properties and thermal conductive properties, for example, copper. The first high-frequency electrode 122 is electrically connected to the control apparatus 60 through a first high-frequency electrode energizing line 124 and a cable 40. Likewise, the second high-frequency electrode 132 is electrically connected to the control apparatus 60 through a second high-frequency electrode energizing line 132 and the cable 40.

For example, when a user operates one of the operation knobs 28, a high-frequency voltage, i.e., high-frequency energy supplied from the control apparatus 60 is applied to the first high-frequency electrode 122 and the second high-frequency electrode 132. In a state that the living tissue is grasped by the grasping portion 26, when the high-frequency voltage is applied to the first holding member 120 and the second holding member 130, the high-frequency voltage is applied to the grasped living tissue. As a result, the living tissue is heated and denatured by an operation of Joule heat.

Heater members 142 are discretely arranged or a sheet-like heater member 142 is arranged on each of a surface of the first high-frequency electrode 122 that does not come into contact with the living tissue and a surface of the second high-frequency electrode 132 that does not come into contact with the living tissue. Each heater member 142 is electrically connected to the control apparatus 60 through each heater member energizing line 144 and the cable 40. For example, when a user operates the operation knobs 28, a voltage is applied to the heater members 142 from the control apparatus 60. When the voltage is applied to the heater members 142, each heater member 142 generates heat. The heat generated by each heater member 142, i.e., thermal energy is transmitted to the first high-frequency electrode 122 and the second high-frequency electrode 132. In a state that the living tissue is being grasped by the grasping portion 26, when the first high-frequency electrode 122 and the second high-frequency electrode 132 have a high temperature, the grasped living tissue is heated, dehydrated, and solidified. It is to be noted that the application of the high-frequency voltage and the heating may be started in response to an operation of a non-illustrated foot switch connected to the control apparatus 60 effected by a user.

As shown in FIG. 2, for example, a plate-like precut blade 152 having a blade on the distal end side is accommodated in the shaft 24 on the distal end side. This precut blade 152 is configured to incise the living tissue which constitutes an intervention site. A first push rod 154 is connected to the proximal end side of the precut blade 152. The first push rod 154 is connected to one of the operation knobs 28. For example, when a user operates one of the operation knobs 28, the first push rod 154 is pushed toward the distal end side. As a result, the precut blade 152 is pushed out between the first holding member 120 and the second holding member 130. In this manner, the precut blade 152 can incise the living tissue held between the first holding member 120 and the second holing member 130.

An artificial collagen sheet 192 is arranged on at least one of upper and lower parallel surfaces of the plate-like precut blade 152 to be slidable with respect to the precut blade 152. A second push rod 156 connected to the operation knobs 28 is provided in the shaft 24 according to this embodiment. For example, the distal end side of the second push rod 156 is connected to the proximal end side of the artificial collagen sheet 192. Alternatively, the artificial collagen sheet 192 may be arranged to cover the second push rod 156. That is, the second push rod 156 may be sticking in the artificial collagen sheet 192. The second push rod 156 is configured to push out the artificial collagen sheet 192 along the precut blade 152. After the precut blade 152 is pushed out between the first holding member 120 and the second holding member 130, when the second push rod 156 is pushed out, the artificial collagen sheet 192 is pushed out between the first holding member 120 and the second holding member 130 along the precut blade 152.

An example of operations of the surgical system 10 according to this embodiment will now be described with reference to a schematic view showing a distal end portion of the surgical device 20. The surgical system 10 according to this embodiment is used for compressing and cauterizing tubular living tissue and welding an inner surface of this tubular living tissue. First, a user operates an input portion of the control apparatus 60 and sets output conditions of the surgical system 10, for example, set electric power as an output of high-frequency energy from each of the first high-frequency electrode 122 and the second high-frequency electrode 132, a target temperature as an output of thermal energy from each heater member 142, a procedure time, and other parameters in advance. Each value may be individually set, or a set of set values associated with an operative procedure may be selected.

The grasping portion 26 and the shaft 24 of the surgical device 20 are inserted into, for example, an abdominal cavity through an abdominal wall. The user operates the operation knobs 28, opens the grasping portion 26, and places tubular living tissue 900 constituting an intervention site between the first holding member 120 and the second holding member 130 as schematically shown in FIG. 3A. As the tubular living tissue 900, for example, an intestinal tract is assumed.

As schematically shown in FIG. 3B, the first holding member 120 and the second holding member 130 lightly grasp the living tissue 900. In this state, the precut blade 152 is pushed out by using the first push rod 154. The precut blade 152 incises the living tissue 900 and is inserted into this living tissue.

Figure 3C:
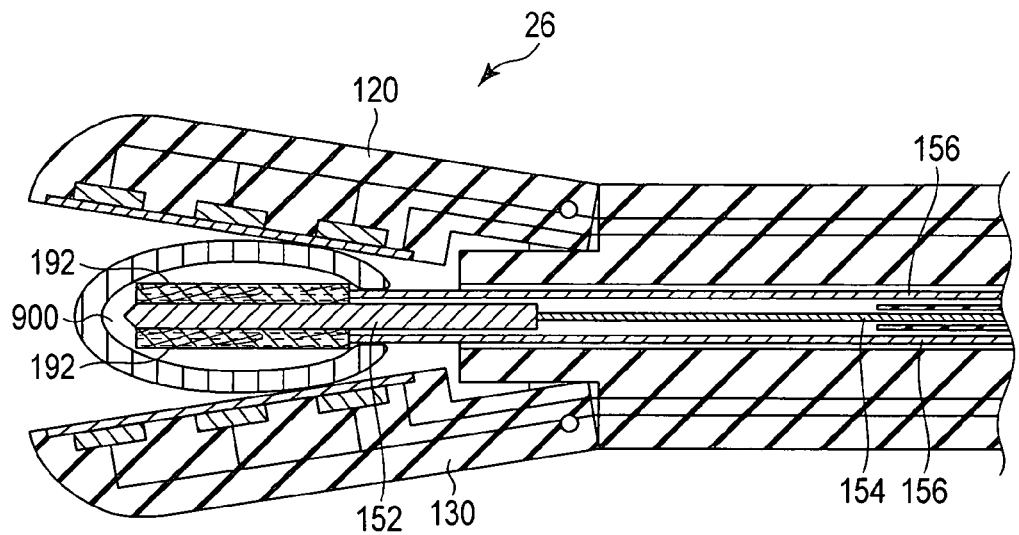
FIG. 3C is a third schematic view for explaining the surgical procedure using the surgical device according to the first embodiment.
Figure 3D:
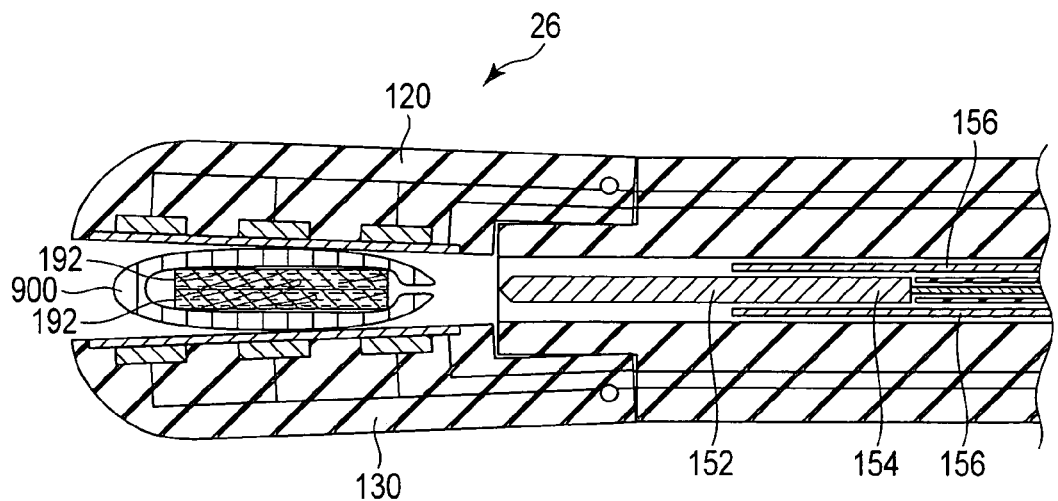
FIG. 3D is a fourth schematic view for explaining the surgical procedure using the surgical device according to the first embodiment.

Then, as schematically shown in FIG. 3C, the second push rods 156 push the artificial collagen sheets 192 into the living tissue 900 along the precut blade 152. Subsequently, as schematically shown in FIG. 3D, the grasping portion 26 is closed, and the precut blade 152, the first push rod 154, and the second push rods 156 are retracted. At this time, the living tissue 900 is sandwiched between the first holding member 120 and the second holding member 130, and it deforms to be compressed. As a result, the artificial collagen sheets 192 are pressed against inner walls of the living tissue 900. Therefore, when the second push rods 156 are retracted, the artificial collagen sheets 192 are disconnected from the second push rods 156, the artificial collagen sheets 192 remain in the living tissue 900, and the second push rods 156 alone are retracted into the shaft 24.

At last, the first holding member 120 and the second holding member 130 are further strongly closed. As a result, the living tissue 900 is compressed, and the artificial collagen sheets 192 are pressed against the inner surfaces of the living tissue. In this state, a high-frequency voltage is first applied between the first high-frequency electrode 122 and the second high-frequency electrode 132. That is, high-frequency energy is applied to the living tissue 900. As a result, the living tissue 900 is denatured by an operation of the thermal energy. At this time, the living tissue 900 and collagen in the artificial collagen sheets 192 are chemically bound. Subsequently, a voltage is applied to the heater members 142, and the first high-frequency electrode 122 and the second high-frequency electrode 132 are heated. That is, thermal energy is applied to the living tissue 900. As a result, the living tissue is dehydrated, and inner surfaces of the living tissue 900, i.e., opposed surfaces of the living tissue 900 are welded in the compressed state.

For example, the two opposed surfaces of the inner walls of the living tissue 900 that are welded in this manner correspond to a first surface and a second surface. For example, the grasping portion 26 functions as a grasping portion that grasps the living tissue. For example, the precut blade 152 functions as an incising portion that incises the living tissue grasped by the grasping portion. For example, the artificial collagen sheets 192 function as a biocompatible material that is chemically bound with the living tissue by application of the high-frequency energy. For example, the second push rods 156 and the precut blade 152 function as an introduction portion that introduces the biocompatible material into a portion between the first surface and the second surface of the incised living tissue. The first high-frequency electrode 122 and the second high-frequency electrode 132 function as an intervention portion configured to apply the high-frequency energy and the thermal energy to the living tissue.

According to this embodiment, the artificial collagen sheets 192 can be easily inserted into a space between portions of the living tissue 900 which are to be welded. As a result, these portions are stably and firmly welded. In this embodiment, the artificial collagen sheets 192 can be assuredly arranged on the surfaces which are to be coated, i.e., desired positions in the living tissue 900 along the precut blade 152. Further, a user can perform the incision of the living tissue 900, the insertion of the artificial collagen sheets 192, the application of the high-frequency voltage, and the heating as a series of operations. As a result, the user can efficiently perform the operations.

It can be considered that, when the artificial collagen sheets 192 are inserted into the portion between the surfaces to be welded in the living tissue, welding becomes stable and firm for the following reason. That is, it is considered that hydrogen bonding contributes to the welding based on the heating including the application of the high-frequency voltage like this embodiment. Here, it is considered that, when portions to be welded are exposed to water, this hydrogen bonding collapses, and bonding force is lowered. On the other hand, it is recognized that, when the artificial collagen sheets are inserted into a part between the portions to be welded, collapse of the hydrogen bonding can be avoided, and the welding becomes stable.

It is to be noted that, in place of the artificial collagen sheets 192, the following tissue prostheses can be used. For example, it is possible to use low-molecular peptide that has a molecular mass of 50 or below based on an extracellular matrix, which contains an amino-acid sequence PHG (proline-histidine-glycine) or an amino-acid sequence PPG (proline-proline-glycine) that is present in collagen or an amino-acid sequence GVP (glycine-valine-proline) that is present in elastin. Further, a polymer like collagen or elastin may be used. Furthermore, a mixture of these materials may be used. When a molecular chain is short, a material is apt to fibrose. Moreover, when the number of terminal amino groups is large, a cross-linking reaction occurs with great frequency. Therefore, it is particularly preferable to use a material having a short molecular chain and many terminal amino groups.

Additionally, it is preferable for each tissue prosthesis to contain thermal cross-linking, fibrosis, and/or chemical cross-linking. Here, the chemical cross-linking preferably includes at least one of aldehyde cross-linking, epoxy cross-linking, carbodiimide cross-linking, isocyanate cross-linking, enzymatic cross-linking, and genipin cross-linking. For example, as a material having the aldehyde cross-linking, there is glutaraldehyde. For example, as a material having the epoxy cross-linking, there is ethylene glycol glycidyl ether. For example, as a material having the carbodiimide cross-linking, there is 1-ethyl-3-(3-dimethyl amino propyl)carbodiimide hydrochloride. For example, as a material having the isocyanate cross-linking, there is hexamethylene diisocyanate. For example, as a material having the enzymatic cross-linking, there is transglutaminase or lysyl oxidase.

Further, it is preferable for a cross-linking agent of the chemical cross-linking agent to have concentration of 0.1 to 20 mol %. This cross-linking agent is preferably added to collagen. It is to be noted that, according to experiments, when the concentration of the cross-linking agent was increased from 1 to 2 mol % even though a cross-linking reaction time is 24 hours or 48 hours, shape maintainability of the tissue prosthesis was improved. Furthermore, when the reaction time of the cross-linking agent was extended from 24 hours to 48 hours even though the concentration of the cross-linking agent is 1 or 2 mol %, the shape maintainability of the tissue prosthesis was improved. In combinations of 1 or 2 mol % as the concentration of the cross-linking agent and 24 hours or 48 hours as the reaction time of the cross-linking agent, the tissue prosthesis had the highest shape maintainability when the concentration of the cross-linking agent was 2 mol % and the reaction time was 48 hours.

Moreover, in regard to the fibrosis, it is preferable for the tissue prosthesis to contain heat-denatured atelocollagen with concentration of 5 to 50 weight %. Additionally, using a polyvalent carboxylic acid for the thermal cross-linking is preferable. It is preferable for the polyvalent carboxylic acid used herein to contain any one of a succinic acid, an adipic acid, a citric acid, a malonic acid, and a fumaric acid. An additive amount of the polyvalent carboxylic acid used for the thermal cross-linking is preferably 0.1 to 5 mol equivalent amount with respect to a total mol amount of a glutamine residue, an asparagine residue, a glutamic acid residue, and an aspartic acid residue contained in the tissue prosthesis. Further, a thermal treatment temperature of the thermal cross-linking is preferably 100 to 150° C.

Modification of First Embodiment

A modification of the first embodiment according to the present invention will now be described with reference to FIG. 4 to FIG. 5E. Here, a difference from the first embodiment will be described, and like reference numbers denote like parts to omit a description thereof. A surgical device 20 according to this modification is different from the surgical device 20 according to the first embodiment in configurations concerning the precut blade 152, the first push rod 154, the second push rods 156, and the artificial collagen sheets 192. A configuration of a grasping portion 26 is the same as that in the first embodiment.

FIG. 4 shows an outline of an example of a configuration of a distal end portion of a surgical device 20 according to this modification. As shown in this drawing, the surgical device 20 according to this modification includes a first cover member 162 and a second cover member 164. The first cover member 162 and the second cover member 164 are accommodated in a shaft 24. The first cover member 162 and the second cover member 164 are combined with each other to have a wedge-like end shape and a hollow. An artificial collagen sheet 192 is arranged in the hollow formed of the first cover member 162 and the second cover member 164.

A first push rod 172 is arranged on the proximal end side of the artificial collagen sheet 192. The first push rod 172 is connected to one of operation knobs 28 and configured to push the artificial collagen sheet 192 toward the distal end side. Further, a second push rod 174 is arranged on the proximal end side of the first cover member 162, and a third push rod 176 is arranged on the proximal end side of the second cover member 164. Each of the second push rod 174 and the third push rod 176 is connected to one of the operation knobs 28, and it is configured to push the first cover member 162 or the second cover member 164 toward the distal end side or retract the same toward the proximal end side.

Operations of the surgical device 20 according to this modification will now be described with reference to the drawings showing an outline of an example of the operations. Here, the illustration of the first holding member 120, the second holding member 130, the shaft 24, and others will be omitted, but the first cover member 162, the second cover member 164, the artificial collagen sheet 192, the first push rod 172, the second push rod 174, and the third push rod 176 with respect to tubular living tissue 900 will be shown, and operations of these members will be explained.

Figure 5A:
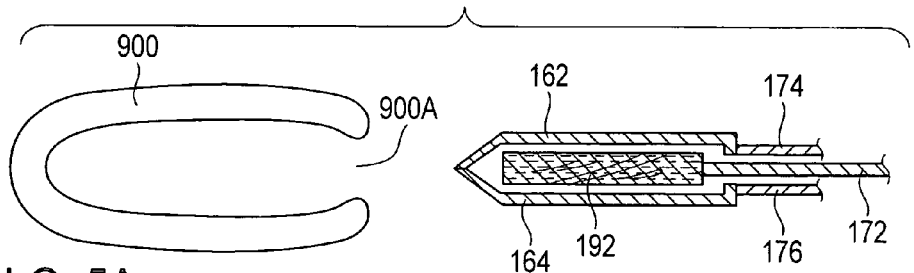
FIG. 5A is a first schematic view for explaining a surgical procedure using the surgical device according to the modification of the first embodiment.

As shown in FIG. 5A, in this modification, a part of the tubular living tissue 900 is incised by non-illustrated another surgical instrument in a different process, and an incised hole 900A is formed. When the living tissue 900 is grasped by the grasping portion 26, the first cover member 162 and the second cover member 164 having the artificial collagen sheet 192 therein are positioned to face the incised hole 900A.

Figure 5B:
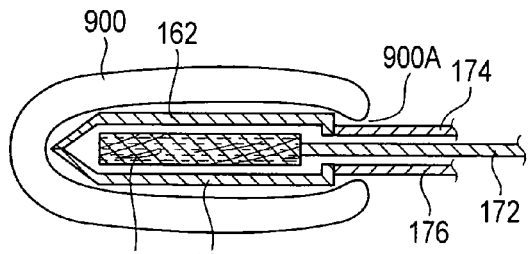
FIG. 5B is a second schematic view for explaining the surgical procedure using the surgical device according to the modification of the first embodiment.

As shown in FIG. 5B, the first cover member 162 and the second cover member 164 having the artificial collagen sheet 192 therein are inserted into the incised hole 900A of the living tissue 900 grasped by the grasping portion 26. Here, the first cover member 162, the second cover member 164, and the artificial collagen sheet 192 are displaced by the second push rod 174, the third push rod 176, and the first push rod 172, respectively.

Figure 5C:
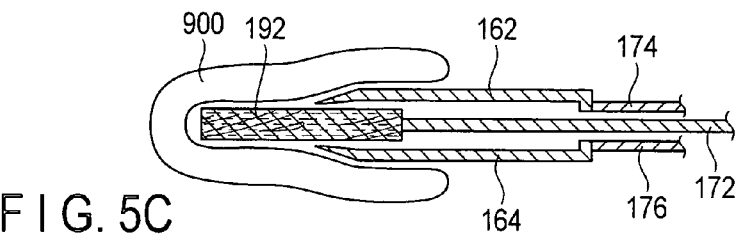
FIG. 5C is a third schematic view for explaining the surgical procedure using the surgical device according to the modification of the first embodiment.

Then, as shown in FIG. 5C, when the second push rod 174 and the third push rod 176 are retracted, the artificial collagen sheet 192 remains in the living tissue 900, and the first cover member 162 and the second cover member 164 are removed from the living tissue 900 in this state. Here, a distal end portion of each of the first cover member 162 and the second cover member 164 has flexibility. Therefore, when a position of the artificial collagen sheet 192 is maintained and the first cover member 162 and the second cover member 164 are retracted toward the proximal end side in this state, the distal end sides of the first cover member 162 and the second cover member 164 are opened. In this manner, the artificial collagen sheet 192 is allowed to remain in the living tissue 900, and the first cover member 162 and the second cover member 164 can be retracted into the shaft 24.

Figure 5D:
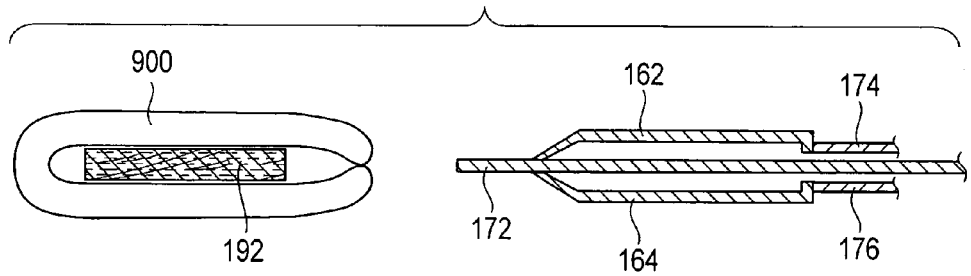
FIG. 5D is a fourth schematic view for explaining the surgical procedure using the surgical device according to the modification of the first embodiment.

Subsequently, as shown in FIG. 5D, the first push rod 172 is retracted. At this time, the living tissue 900 is sandwiched between the first holding member 120 and the second holding member 130 and has a compressed shape, and the artificial collagen sheet 192 is pressed against an inner wall of the living tissue 900. Therefore, the first push rod 172 is disconnected from the artificial collagen sheet 192, the artificial collagen sheet 192 remains in the living tissue 900, and the first push rod 172 alone is retracted into the shaft.

Figure 5E:
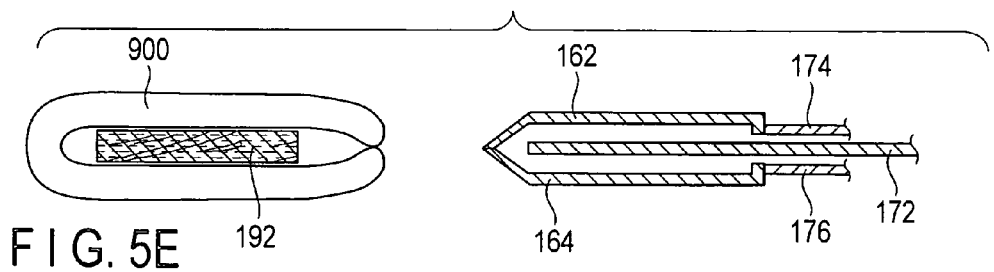
FIG. 5E is a fifth schematic view for explaining the surgical procedure using the surgical device according to the modification of the first embodiment.

Then, as shown in FIG. 5E, the living tissue 900 containing the artificial collagen sheet 192 inside is strongly grasped by the first holding member 120 and the second holding member 130, application of a high-frequency voltage and heating are finally carried out, and the living tissue 900 is welded. In this manner, for example, the first cover member 162, the second cover member 164, the first push rod 172, the second push rod 174, and the third push rod 176 function as an introduction portion as a whole.

According to this embodiment, like the first embodiment, the artificial collagen sheet 192 can be easily inserted into a space between the parts of the living tissue 900 to be welded. As a result, a reduction in welding force caused due to exposure of the portion to be welded to water can be suppressed, and stable and strong welding can be realized.

It is to be noted that the distal end portions of the first cover member 162 and the second cover member 164 may be sharpened so that the first cover member 162 and the second cover member 164 can function as a cutter. When the first cover member 162 and the second cover member 164 have the function as a cutter, a user can insert the first cover member 162 and the second cover member 164 containing the artificial collagen sheet 192 therein into the living tissue 900 without additionally making an incision in the living tissue 900. That is, in this case, the incision of the living tissue 900, the insertion of the artificial collagen sheet 192, the application of a high-frequency voltage, and the heating can be carried out as a series of operations. As a result, the user can efficiently perform the operations. Moreover, the first cover member 162 and the second cover member 164 can be integrated, and either the second push rod 174 or the third push rod 176 that displaces each cover member can be selectively used.

Second Embodiment

Figure 6:
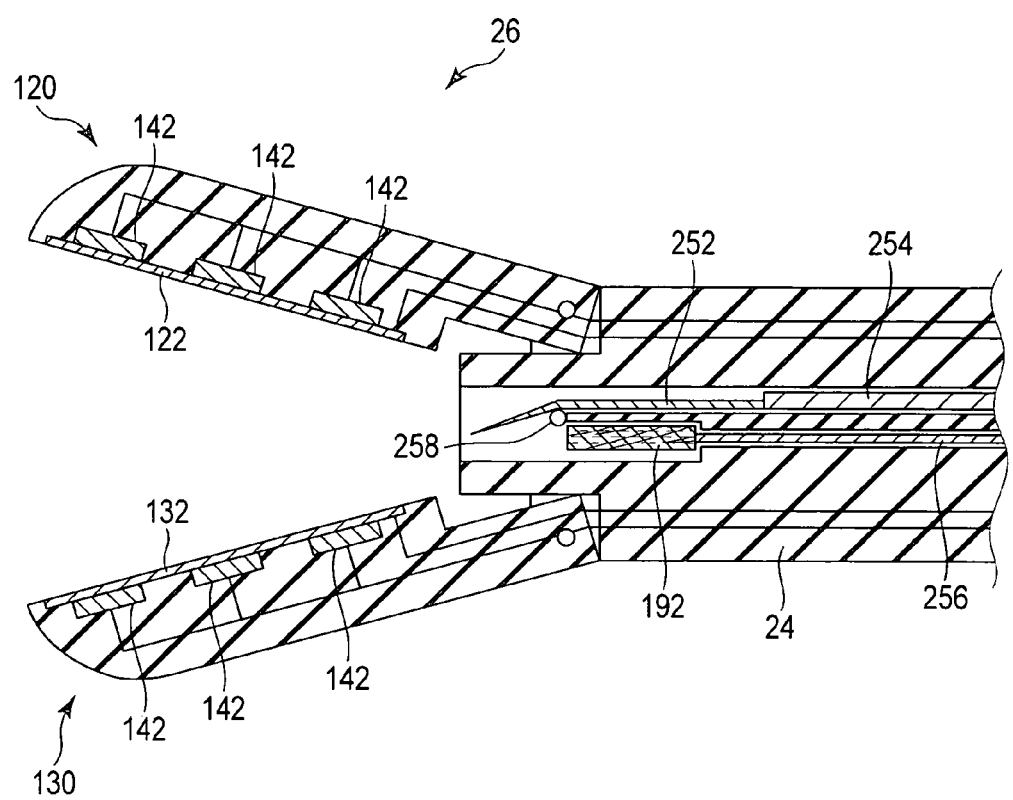
FIG. 6 is a view showing a structural example of an end portion of the surgical device according to a second embodiment.

A second embodiment according to the present invention will now be described with reference to FIG. 6 to FIG. 8. Here, a difference from the first embodiment will be described, and like reference numbers denote like parts to omit a description thereof. FIG. 6 shows an outline of an example of a configuration of a distal end portion of a surgical device 20 according to this embodiment. As shown in this drawing, the surgical device 20 according to this embodiment includes a precut blade 252, a first push rod 254, a second push rod 256, and a stopper 258 in place of the precut blade 152, the first push rod 154, and the second push rod 156 according to the first embodiment. A configuration of a grasping portion 26 is the same as that in the first embodiment.

In this embodiment, the precut blade 252 has a sharp blade at a distal end. The first push rod 254 is connected to the proximal end side of the precut blade 252. The first push rod 254 is displaced in tandem with operation knobs 28. That is, when a user operates the operation knobs 28, the first push rod 254 is displaced to the distal end side and the proximal end side, and the precut blade 252 is also displaced to the distal end side and the proximal end side. This precut blade 252 is configured to incise living tissue grasped by the grasping portion 26. Further, a distal end of the precut blade 252 has a bent shape. The precut blade 252 is configured to be displaced along the stopper 258.

An artificial collagen sheet 192 is arranged on the distal end side of the second push rod 256. The distal end side of the second push rod 256 is connected to the proximal end side of the artificial collagen sheet 192. The second push rod 256 is also displaced in cooperation with the operation knobs 28. When the user operates the operation knobs 28, the second push rod 256 is displaced toward the distal end side, and the artificial collagen sheet 192 is also displaced toward the distal end side. The second push rod 256 is configured to insert the artificial collagen sheet 192 into the living tissue incised by the precut blade 252. It is to be noted that the first push rod 254 and the second push rod 256 are preferably arranged in parallel to each other, for example.

Figure 7A:
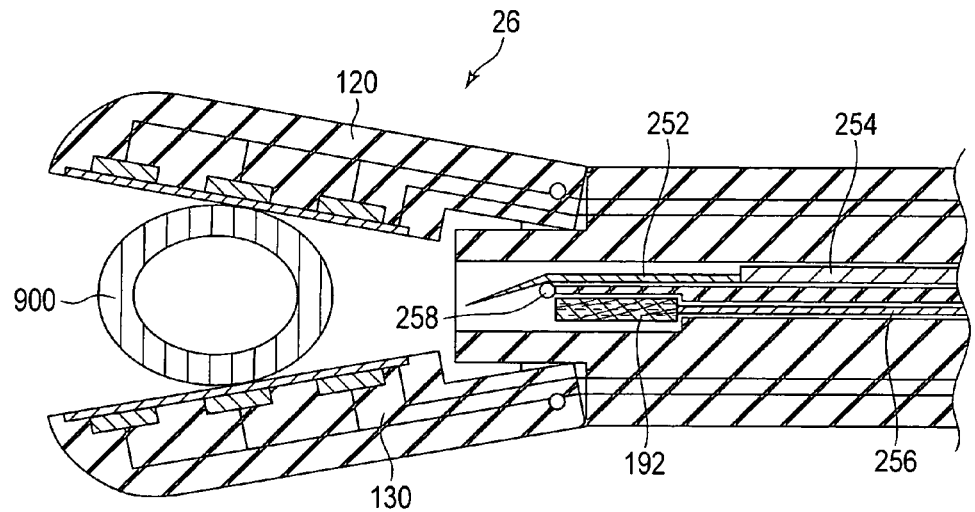
FIG. 7A is a first schematic view for explaining a surgical procedure using the surgical device according to the second embodiment.
Figure 7B:
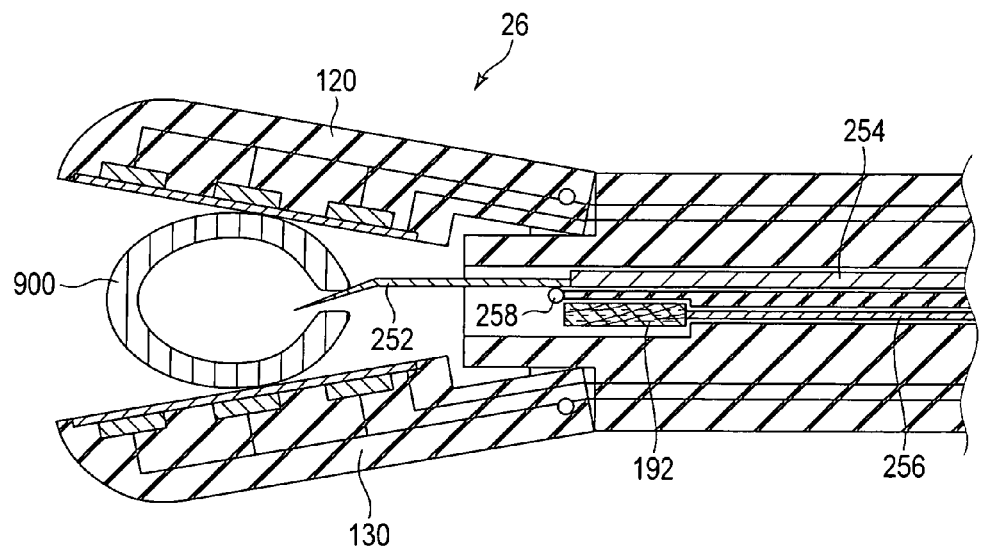
FIG. 7B is a second schematic view for explaining the surgical procedure using the surgical device according to the second embodiment.

An example of operations of the surgical device 20 according to this embodiment will now be described with reference to the drawings showing the outline. As shown in FIG. 7A, the user operates the surgical device 20 and lightly grasps tubular living tissue 900 which constitutes an intervention site by using a first holding member 120 and a second holding member 130 of the grasping portion 26 in such a manner that the living tissue 900 is not compressed. Then, as shown in FIG. 7B, the precut blade 252 is pushed toward the distal end side by manipulation of the operation knobs 28 by the user. The precut blade 252 incises the living tissue 900 grasped by the grasping portion 26.

As shown in FIG. 7C, the precut blade 252 is retracted toward the proximal end side. At this time, the precut blade 252 is linearly deformed by the stopper 258. As a result, there is no obstacle in a region connecting the artificial collagen sheet 192 with an incised hole 900A provided in the living tissue 900 by a straight line. Here, the second push rod 256 is displaced toward the distal end side. That is, the artificial collagen sheet 192 is pushed toward the distal end side and inserted into the living tissue 900 from the incised hole 900A formed by the precut blade 252.

As shown in FIG. 7D, the first holing member 120 and the second holding member 130 strongly compress the living tissue 900, and the second push rod 256 is retracted toward the proximal end side. At this time, the living tissue 900 is compressed, and an inner wall of the living tissue 900 is pressed against the artificial collagen sheet 192. Therefore, when the second push rod 256 is retracted, the second push rod 256 is disconnected from the artificial collagen sheet 192, and the artificial collagen sheet 192 remains in the living tissue 900. In this state, the grasping portion 26 applies a high-frequency voltage to the living tissue 900 and heats the living tissue 900. Thus, the living tissue 900 is welded at a portion grasped by the grasping portion 26. In this manner, for example, the precut blade 252 functions as an incising portion. For example, the second push rod 256 functions as an introduction portion.

In this embodiment, like the first embodiment, the surgical device 20 can easily insert the artificial collagen sheet 192 into a space between the portions of the living tissue 900 which are to be welded. As a result, a reduction in welding force caused due to exposure of the portions to be welded to water can be suppressed, and stable welding can be realized. Furthermore, the user can perform the incision of the living tissue 900, the insertion of the artificial collagen sheet 192, the application of the high-frequency voltage, and the heating as a series of operations, and he/she can efficiently carry out the operations.

It is to be noted that, in this embodiment, the artificial collagen sheet 192 has a wedge-shaped distal end portion as shown in FIG. 8 and the hard distal end portion is preferable. When the hard wedge-like shape is provided, the artificial collagen sheet 192 can be easily inserted into the living tissue 900 from the incised hole 900A.

Modification of Second Embodiment

A modification of the second embodiment will now be described. Here, a difference from the second embodiment will be explained. A surgical device 20 according to this modification does not have a precut blade 252 and a first push rod 254. Other structures are the same as those in the surgical device 20 according to the second embodiment.

A user incises living tissue 900 which constitutes an intervention site by, for example, a cautery knife in advance. The user grasps an incised part of the living tissue 900 with a first holding member 120 and a second holding member 130 of a grasping portion 26. Then, like the second embodiment, operation knobs 28 are operated, a second push rod 256 is pushed toward the distal end side, and an artificial collagen sheet 192 is inserted into the living tissue 900. The second push rod 256 is retracted, the living tissue 900 is strongly grasped by using the first holding member 120 and the second holding member 130, a high-frequency voltage is applied to the living tissue 900, and the living tissue 900 is heated. In this manner, the surgical device 20 welds the living tissue 900.

It is to be noted that, in this modification, the operation of grasping the living tissue 900 by using the grasping portion 26 and the operation of pushing the second push rod 256 to insert the artificial collagen sheet 192 may be allowed to interlock with each other and configured as a series of operations.

In this embodiment, likewise, the surgical device 20 can easily insert the artificial collagen sheet 192 into a space between the portions of the living tissue 900 to be welded. Moreover, the user can perform the insertion of the artificial collagen sheet 192, the application of the high-frequency voltage, and the heating as a series of operations, and he/she can efficiently carry out the operations.

Third Embodiment

Figure 9:
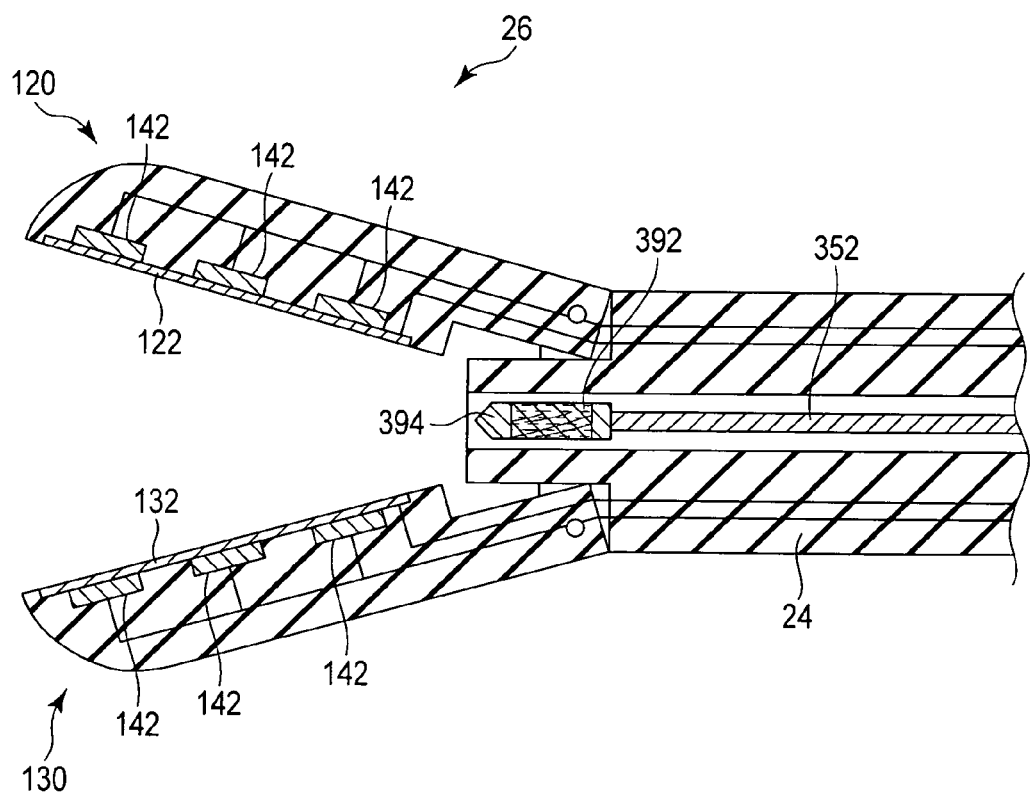
FIG. 9 is a view showing a structural example of an end portion of the surgical device according to a third embodiment.

A third embodiment will now be described with reference to FIG. 9 to FIG. 11D. Here, a difference from the first embodiment will be described, and like reference numbers denote like parts to omit a description thereof. FIG. 9 shows an outline of an example of a configuration of a distal end portion of a surgical device 20 according to this embodiment. As shown in this drawing, a configuration of a grasping portion 26 is the same as that in the first embodiment. A casing 394 configured to include artificial collagen 392 is provided in a shaft 24 of the surgical device 20 according to this embodiment. The casing 394 is made of, for example, polylactate. The casing 394 is harder than living tissue, and its distal end side has a sharp shape. A push rod 352 is connected to the proximal end side of the casing 394. When the push rod 352 moves in the longitudinal direction, the casing 394 is displaced toward the distal end side and the proximal end side. The casing 394 is pushed to a space between a first holding member 120 and a second holding member 130.

FIG. 10A shows a portion corresponding to the casing 394 and the push rod 352, and FIG. 10B shows a cross-sectional view taken along a line 10B-10B in FIG. 10A. As shown in these drawings, the casing 394 has a thick tabular shape having a sharp wedge-like distal end. In the casing 394, a through hole 395 which accounts for the majority of an area of a plane of the casing 394 is provided. The through hole 395 is filled with the artificial collagen 392.

An example of operations of the casing 394 and the push rod 352 with respect to the living tissue 900 will now be described with reference to drawings that show the outline. It is to be noted that, in these drawings, the illustration of the first holding member 120, the second holding member 130, the shaft 24, and others is omitted.

Figure 11A:
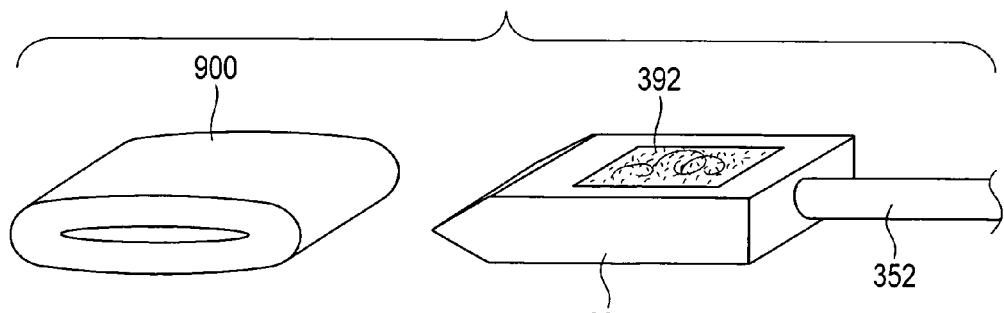
FIG. 11A is a first schematic view for explaining a surgical procedure using the surgical device according to the third embodiment.
Figure 11B:
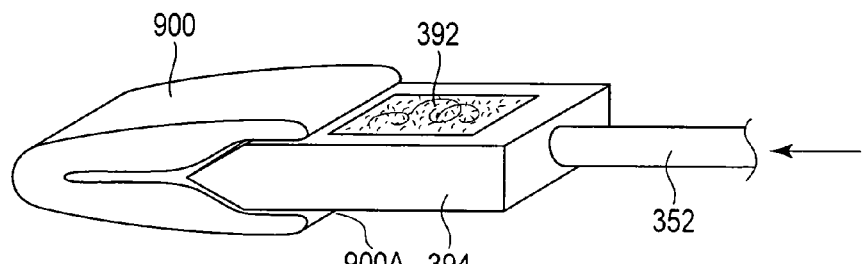
FIG. 11B is a second schematic view for explaining the surgical procedure using the surgical device according to the third embodiment.

As shown in FIG. 11A, the living tissue 900 is grasped by the grasping portion 26, and the living tissue 900 is placed on the distal end side of the casing 394 containing the artificial collagen 392. When the push rod 352 is pushed toward this living tissue 900, the casing 394 containing the artificial collagen 392 is moved. Since the casing 394 has the sharp wedge-like distal end harder than the living tissue 900, the casing 394 incises the living tissue 900 and is inserted into the living tissue 900 while forming an incised hole 900A as shown in FIG. 11B.

Figure 11C:
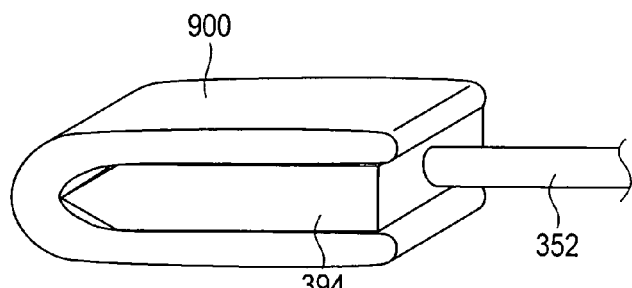
FIG. 11C is a third schematic view for explaining the surgical procedure using the surgical device according to the third embodiment.
Figure 11D:
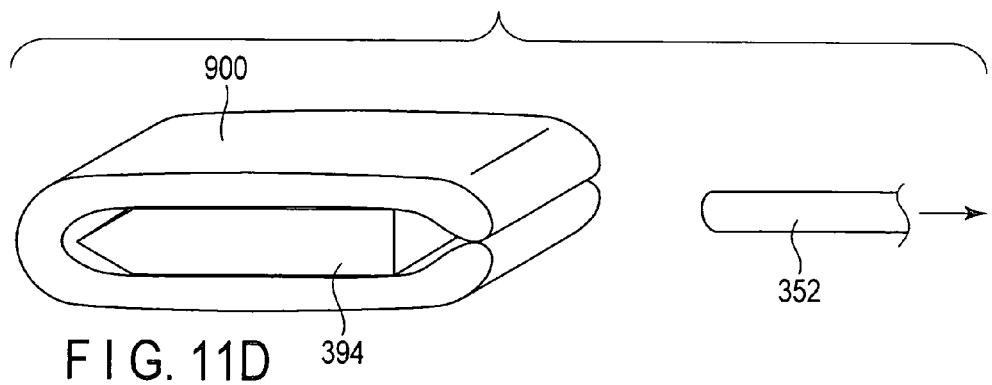
FIG. 11D is a fourth schematic view for explaining the surgical procedure using the surgical device according to the third embodiment.

When the casing 394 is inserted in the living tissue 900 as shown in FIG. 11C, the push rod 352 is retracted toward the proximal end side as shown in FIG. 11D. At this time, since the artificial collagen 392 is pressed against an inner wall of the living tissue 900, the casing 394 including the artificial collagen 392 is disconnected from the push rod 352. As a result, the casing 394 including the artificial collagen 392 remains in the living tissue 900, and the push rod 352 alone is retracted. Then, the living tissue 900 is strongly grasped by using the grasping portion 26, a high-frequency voltage is applied to the living tissue 900, and the living tissue 900 is heated. As a result, the living tissue 900 is welded. It is to be noted that the casing 394 formed of polylactate is taken into the living tissue 900, or it is dissolved and eluted off.

In this manner, for example, the casing 394 and the push rod 352 function as an introduction portion.

In this embodiment, like the first embodiment, the surgical device 20 can easily insert the artificial collagen 392 into a space between the parts of the living tissue 900 to be welded. As a result, a reduction in welding force caused due to exposure of the parts to be welded to water can be suppressed, and stable welding can be realized. Further, the user can perform the incision of the living tissue 900, the insertion of the artificial collagen 392, the application of the high-frequency voltage, and the heating as a series of operations, and he/she can efficiently carry out the operations.

Fourth Embodiment

A fourth embodiment according to the present invention will now be described with reference to FIG. 12 and FIG. 13. Here, a difference from the first embodiment will be explained, and like reference numbers denote like parts to omit a description thereof. A surgical device 20 according to this embodiment administers powdered artificial collagen 490 into living tissue 900 which constitutes an intervention site.

FIG. 12 shows an outline of an example of a configuration of a distal end portion of the surgical device 20 according to this embodiment. A configuration of a grasping portion 26 is equal to that in the first embodiment. The surgical device 20 according to this embodiment includes a discharger 452 that discharges the powdered artificial collagen 490. A push rod 454 is provided on the proximal end side of the discharger 452. The push rod 454 is connected to operation knobs 28, and displacing the push rod 454 to the distal end side and the proximal end side enables the discharger 452 to be displaced to the distal end side and the proximal end side. The discharger 452 is configured to be pushed to a space between a first holding member 120 and a second holding member 130.

The distal end side of the discharger 452 has a sharp wedge-like shape. Discharge holes 453 through which the powdered artificial collagen 490 passes are formed in the discharger 452. The push rod 454 also has a hollow. The discharge holes 453 and the hollow of the push rod 454 are connected, and these members are connected to a non-illustrated pump. When a positive pressure is applied by the non-illustrated pump, the powdered artificial collagen 490 filling the discharge holes 453 is discharged from the discharge holes 453 in the discharger 452.

FIG. 13 shows an outline of an example of a use state of the surgical device 20 according to this embodiment. First, the grasping portion 26 grasps the living tissue 900. Then, when the push rod 454 is operated, the discharger 452 is pressed against the living tissue 900. Since the distal end of the discharger 452 has the sharp wedge-like shape, the living tissue 900 is incised by the discharger 452. Further, the discharger 452 is inserted into the living tissue 900. When the discharger 452 is inserted in the living tissue 900, the discharger 452 discharges the powdered artificial collagen 490 from the discharge holes 453. Thereafter, the push rod 454 is operated, whereby the discharger 452 is retracted from the living tissue 900. At last, the living tissue 900 is strongly grasped by the grasping portion 26, a high-frequency voltage is applied to the living tissue 900, and the living tissue 900 is heated and welded.

In this embodiment, like the first embodiment, the surgical device 20 can easily insert the powdered artificial collagen 490 into a space between the parts of the living tissue 900 to be welded. As a result, a reduction in welding force caused due to exposure of the parts to be welded to water can be suppressed, and the stable welding can be realized. Furthermore, a user can perform the incision of the living tissue 900, the insertion of the powdered artificial collagen 490, the application of the high-frequency voltage, and the heating as a series of operations, and he/she can efficiently carry out the operations. It is to be noted that, in place of the powdered artificial collagen 490, liquid artificial collagen can be used.

Fifth Embodiment

A fifth embodiment according to the present invention will now be described with reference to FIG. 14 and FIG. 15. Here, a difference from the second embodiment will be explained, and like reference numbers denote like parts to omit a description thereof. In a surgical device 20 according to this embodiment, as shown in FIG. 14 that schematically depicts an example, a first suction hole 528 is provided in a first holding member 120, and a second suction hole 538 is provided in a second holding member 130. The first suction hole 528 has one end functioning as a through hole on a first high-frequency electrode 122 side that comes into contact with living tissue and the other end connected to a non-illustrated suction unit. Likewise, the second suction hole 538 has one end functioning as a through hole on a second high-frequency electrode 132 side that comes into contact with the living tissue and the other end connected to the non-illustrated suction unit. The first suction hole 528 and the second suction hole 538 are arranged to avoid a structure such as a heater member 142. Other structures are the same as those in the surgical device 20 according to the second embodiment.

An example of operations of the surgical device 20 according to this embodiment will now be described with reference to FIG. 15. In this embodiment, first, the first holding member 120 and the second holding member 130 grasp living tissue 900. Then, a precut blade 252 is pressed against the living tissue 900 and incises the living tissue 900. The precut blade 252 is retracted, then air in the first suction hole 528 and the second suction hole 538 is suctioned by a non-illustrated suction unit, and a negative pressure is formed in each of the first suction hole 528 and the second suction hole 538. As a result, the living tissue 900 is adsorbed to the first holding member 120 and the second holding member 130. In this state, the grasping portion 26 is slightly opened. As a result, the living tissue 900 is pulled by the first holding member 120 and the second holding member 130, and an incised hole of the living tissue is opened. An artificial collagen sheet 192 provided at the distal end of a second push rod 256 is inserted from the opened incised hole.

When the artificial collagen sheet 192 is inserted, the first holding member 120 and the second holding member 130 are strongly closed, and the second push rod 256 is retracted. The artificial collagen sheet 192 is pressed against an inner wall of the living tissue 900 and remains in the living tissue 900, and the second push rod 256 alone is retracted. The negative pressure in each of the first suction hole 528 and the second suction hole 538 is released. The grasping portion 26 applies a high-frequency voltage to the living tissue 900 and performs heating. With these operations, the living tissue 900 is welded.

In this embodiment, likewise, the living tissue 900 can be incised, and the artificial collagen sheet 192 can be easily inserted into the living tissue 900. As a result, parts as a welding target can be stably welded.

First Modification of Fifth Embodiment

A first modification of the fifth embodiment will now be described with reference to FIG. 16 and FIG. 17. Here, a difference from the fifth embodiment will be explained, and like reference numbers denote like parts to omit a description thereof.

Figure 16:
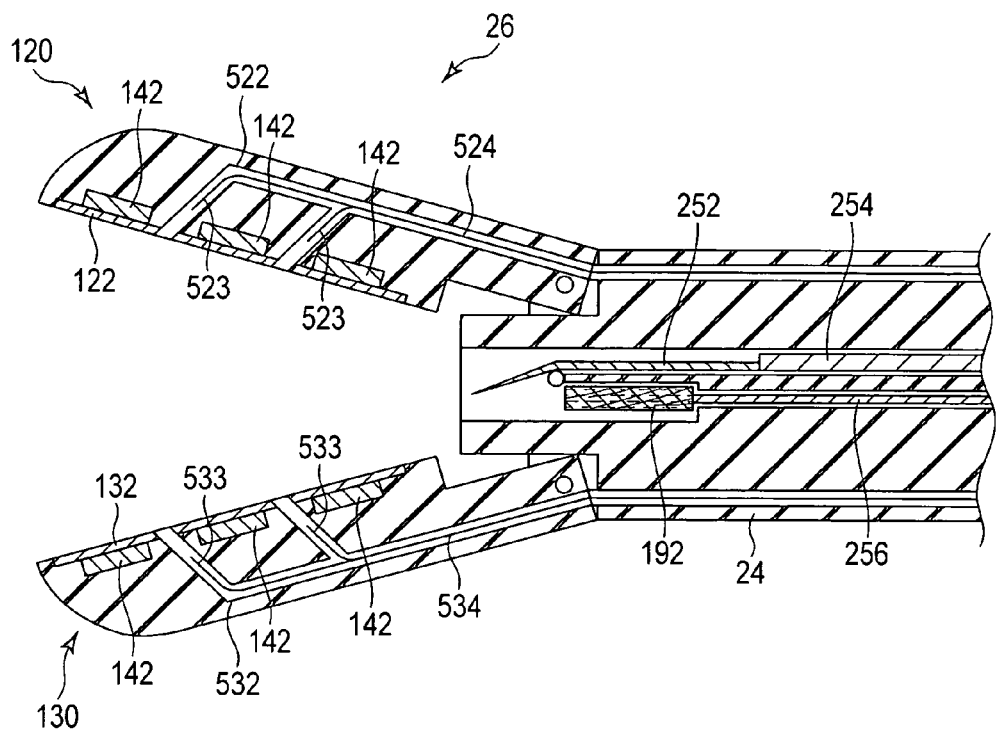
FIG. 16 is a view showing a structural example of an end portion of the surgical device according to a first modification of the fifth embodiment.
Figure 17:
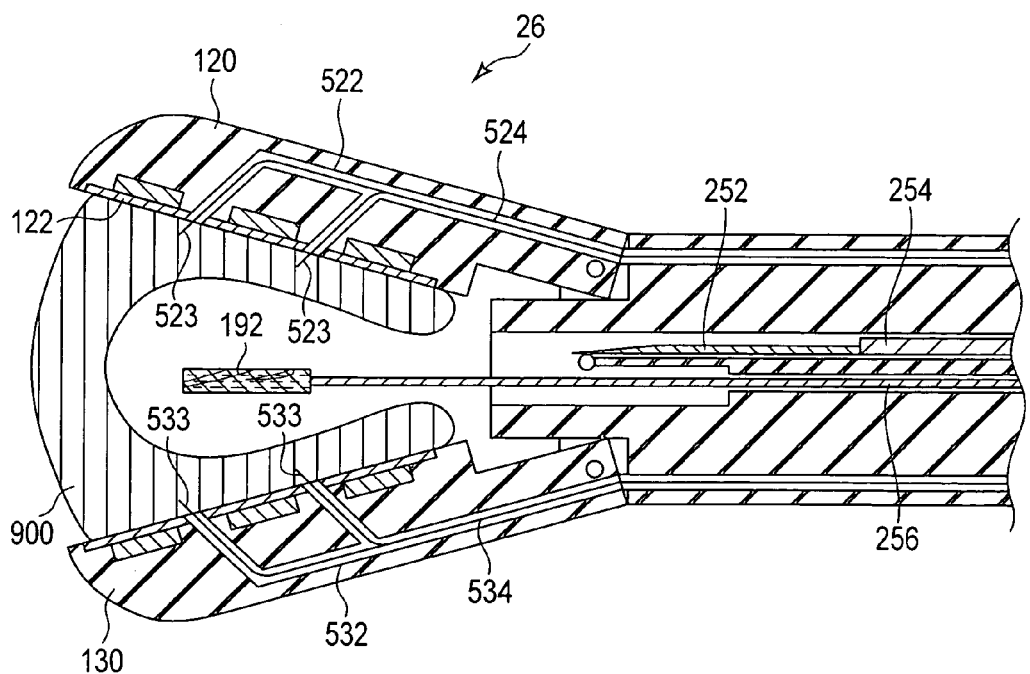
FIG. 17 is a schematic view for explaining a surgical procedure using the surgical device according to the first modification of the fifth embodiment.

As shown in FIG. 16 that schematically depicts an example, a first holding member 120 according to this modification includes a first needle threading hole 522. One end of the first needle threading hole 522 has opening portions on a first high-frequency electrode 122 side that comes into contact with living tissue. The other end of the first needle threading hole 522 is placed in a handle 22 through a shaft 24. An operation wire 524 having flexible needles 523 at distal ends thereof is threaded into the first needle threading hole 522. The needles 523 are arranged near the respective opening portions of the first needle threading hole 522 on the first high-frequency electrode 122 side. The operation wire 524 is displaced along its longitudinal direction by operations of the handle 22 performed by a user.

Likewise, a second holding member 130 includes a second needle threading hole 532. One end of the second needle threading hole 532 has opening portions on a high-frequency electrode 132 side. The other end of the second needle threading hole 532 is placed in the handle 22 through the shaft 24. An operation wire 534 having flexible needles 533 at distal ends thereof is threaded into the second needle threading hole 532. The needles 533 are arranged near the respective opening portions of the second needle threading hole on the second high-frequency electrode 132 side. The operation wire 534 is displaced along its longitudinal direction by operations of the handle 22 performed by a user. With the above-described configuration, the needles 523 and the needles 533 are protruded or retracted from the surfaces of the first high-frequency electrode 122 and the second high-frequency electrode 132.

An example of operations of the surgical device 20 according to this embodiment will now be described. In this embodiment, first, the first holding member 120 and the second holding member 130 grasp living tissue 900. Then, a precut blade 252 is pressed against the living tissue 900 and incises the living tissue 900. The precut blade 252 is retracted, then the operation wire 524 and the operation wire 534 are pushed out, the needles 523 protrude from the first high-frequency electrode 122, and the needle 533 protrude from the second high-frequency electrode 132.

The needles 523 and the needles 533 are stuck into a surface of the living tissue 900. In this state, the grasping portion 26 is slightly opened. As a result, the living tissue 900 is pulled by the first holding member 120 and the second holding member 130, and an incised hole of the living tissue is opened. As schematically shown in FIG. 17, an artificial collagen sheet 192 provided at a distal end of a second push rod 256 is inserted from the opened incised hole.

When the artificial collagen sheet 192 is inserted, the first holding member 120 and the second holding member 130 are strongly closed, and the second push rod 256 is retracted. The artificial collagen sheet 192 is pressed against an inner wall of the living tissue 900 and remains in the living tissue 900, and the second push rod 256 alone is retracted. Further, the operation wire 524 and the operation wire 534 are retracted, and the needles 523 and the needles 533 are removed from the living tissue 900. At last, the grasping portion 26 applies a high-frequency voltage to the living tissue 900 and performs heating. As a result, the living tissue 900 is welded.

In this embodiment, likewise, the surgical device 20 can incise the living tissue 900 and easily insert the artificial collagen sheet 192 into the living tissue 900. As a result, the parts as a welding target can be stably welded.

Second Modification of Fifth Embodiment

A second modification of the fifth embodiment will now be described with reference to FIG. 18 and FIG. 19. Here, a difference from the fifth embodiment will be explained, and like reference numbers denote like parts to omit a description thereof. As shown in FIG. 18 which is a schematic view of an example, in this modification, there is provided an air tube 580 which is arranged to puncture living tissue 900 grasped by a grasping portion 26 from the distal end side of the grasping portion and supplies air into the living tissue 900. Further, a surface of each of a first high-frequency electrode 122 of a first holding member 120 and a second high-frequency electrode 132 of a second holding member 130 that comes into contact with the living tissue 900 is a surface having high friction with respect to the living tissue 900.

Operations of a surgical device 20 according to this embodiment will now be described. In this embodiment, first, the living tissue 900 is grasped by the first holding member 120 and the second holding member 130. Then, a precut blade 252 is pressed against the living tissue 900, and the living tissue 900 is incised. The precut blade 252 is retracted, and then the first holding member 120 and the second holding member 130 are slightly opened as shown in FIG. 18. Here, the air tube 580 makes a puncture from the distal end side of the grasping portion 26. Then, air is blown into the living tissue 900 from the air tube 580. As a result, as schematically shown in FIG. 19, an incised hole of the living tissue is opened. At this time, since the surface of each of the first high-frequency electrode 122 and the second high-frequency electrode 132 has high friction with respect to the living tissue, the living tissue 900 is maintained with the incised hole being opened. An artificial collagen sheet 192 provided at the distal end of a second push rod 256 is inserted from the opened incised hole.

When the artificial collagen sheet 192 is inserted, blowing of air from the air tube 580 is stopped, and the air tube is removed. The first holding member 120 and the second holding member 130 are strongly closed, and the second push rod 256 is retracted. The artificial collagen sheet 192 is pressed against an inner wall of the living tissue 900 and remains in the living tissue 900, and the second push rod 256 alone is retracted. At last, the grasping portion 26 applies a high-frequency voltage to the living tissue 900 and further perform heating. Therefore, the living tissue 900 is welded.

According to this embodiment, likewise, the living tissue 900 can be incised, and the artificial collagen sheet 192 can be easily inserted into the living tissue 900. As a result, parts as a welding target can be stably welded.

Sixth Embodiment

A sixth embodiment according to the present invention will now be described with reference to FIG. 20 to FIG. 21C. Here, a difference from the first embodiment will be explained, and like reference numbers denote like parts to omit a description thereof. A surgical device 20 according to this embodiment does not have the precut blade 152, the first push rod 154, the artificial collagen sheet 192, and the second push rod 156. Instead, the surgical device 20 according to this embodiment is configured to form through holes so that artificial collagen can penetrate through living tissue 900.

Figure 20:
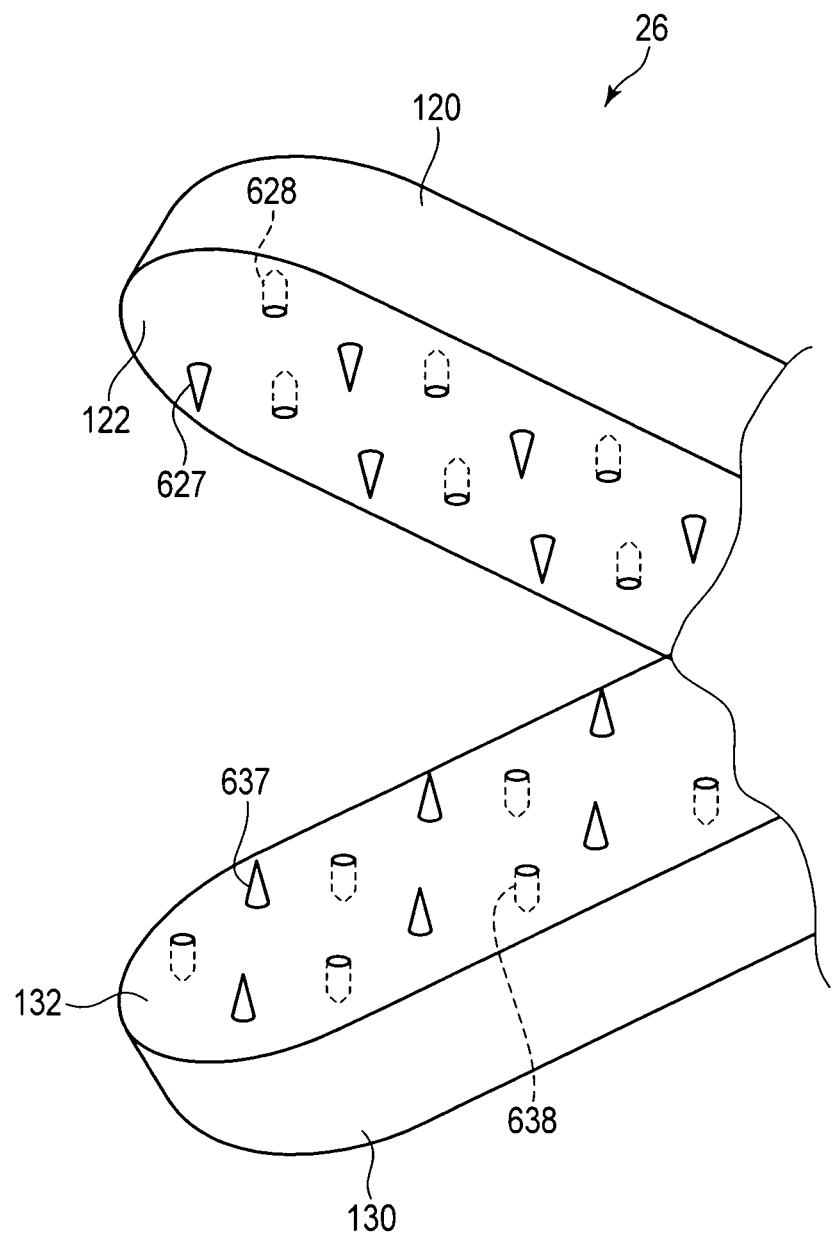
FIG. 20 is a view showing a structural example of an end portion of the surgical device according to a sixth embodiment.

To form through holes in the living tissue 900, as schematically shown in FIG. 20 that shows an example, protruding portions 627 and concave portions 628 are provided on a surface of a first high-frequency electrode 122 facing a second high-frequency electrode 132. Likewise, protruding portions 637 and concave portions 638 are provided on a surface of the second high-frequency electrode 132 facing the first high-frequency electrode 122. Each concave portion 638 of the second high-frequency electrode 132 is provided at a position facing each protruding portion 627 of the first high-frequency electrode 122, and each protruding portion 637 of the second high-frequency electrode 132 is provided at a position facing each concave portion 628 of the first high-frequency electrode 122.

Figure 21A:
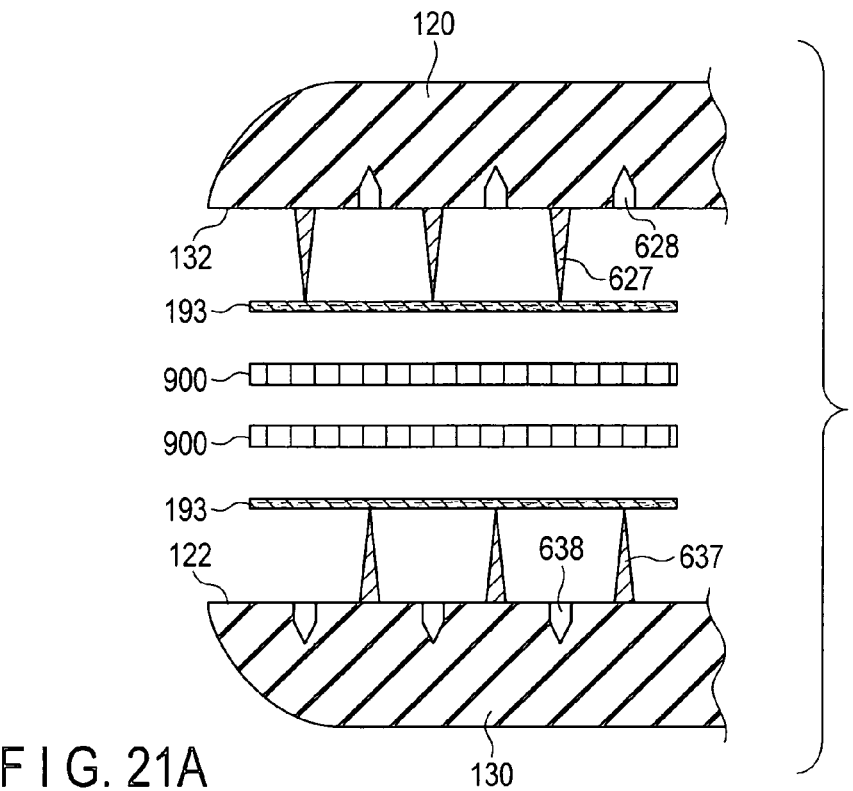
FIG. 21A is a first schematic view for explaining a surgical procedure using the surgical device according to the sixth embodiment.
Figure 21B:
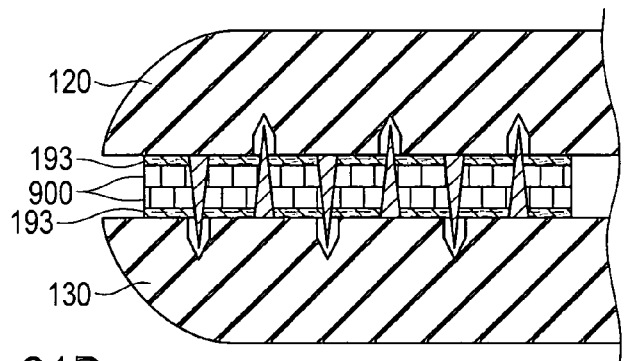
FIG. 21B is a second schematic view for explaining the surgical procedure using the surgical device according to the sixth embodiment.

An example of operations of the surgical device 20 according to this embodiment will now be described with reference to drawings that show the outline. At the time of use, an artificial collagen sheet 193 is arranged on each of the first high-frequency electrode 122 having the protruding portions 627 and the concave portions 628 and the second high-frequency electrode 132 having the protruding portions 637 and the concave portions 638. As shown in FIG. 21A, living tissue 900 is placed between a first holding member 120 and a second holding member 130 each having the artificial collagen sheet 193 provided thereon. Subsequently, as shown in FIG. 21B, when the first holding member 120 and the second holding member 130 are strongly closed, the protruding portions 627 and the protruding portions 637 make a puncture into the artificial collagen sheets 193 and the living tissue 900. At this time, the protruding portions 627 are accommodated in the concave portions 638, and the protruding portions 637 are accommodated in the concave portions 628.

Here, a grasping portion 26 applies a high-frequency voltage to the living tissue 900 and then heats this tissue. As a result, the artificial collagen sheets 193 are dissolved by heat, and the dissolved collagen penetrates through the living tissue 900 via the protruding portions 627 and the protruding portions 637. The application of the high-frequency voltage and the heating enable welding of the living tissue, and the surgical procedure is completed.

Figure 21C:
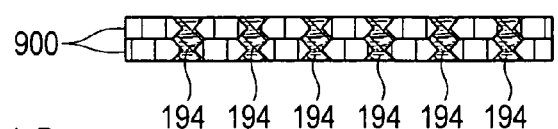
FIG. 21C is a third schematic view for explaining the surgical procedure using the surgical device according to the sixth embodiment.

As a result, as shown in FIG. 21C, anchors 194 made of the artificial collagen are formed, the welding of the living tissue 900 becomes strong. As described above, for example, the protruding portions 627 and 637 function as puncture portions which make a Puncture into a biocompatible material arranged outside the living tissue in a contact manner and the living tissue at the same time.

According to this embodiment, for example, as different from the first embodiment, even if the collagen sheets are not inserted into the living tissue, the artificial collagen sheets 193 can be arranged on the grasp surfaces of the first holding member 120 and the second holding member 130, and the artificial collagen can be introduced to surfaces to be welded in the living tissue 900. As a result, even if moisture is present in the surfaces to be welded, a reduction in welding force caused due to this moisture can be suppressed. Further, since an anchoring effect of the collagen that has penetrated through the living tissue 900 enables mechanically maintaining the welded state of the living tissue 900, strong welding can be realized.

In this embodiment, there has been illustrated the example where the conical protruding portions 627 are fixed on the surface of the first high-frequency electrode 122 and the conical protruding portions 637 are fixed on the surface of the second high-frequency electrode 132. The shape of the protruding portions 627 and 637 is not restricted to the conical shape. The protruding portions 627 and 637 may have any shape as long as their distal ends are sharpened to make a puncture through the living tissue 900. For example, each of the protruding portions 627 and 637 may have a quadrangular pyramid shape, a tabular shape, or a coil-like shape. Furthermore, the protruding portions 627 and 637 do not have to be fixed on the first high-frequency electrode 122 and the second high-frequency electrode 132, respectively. For example, the protruding portions 627 and 637 may be displaced to protrude from the first holding member 120 and the second holding member 130 or to be accommodated in the first holding member 120 and the second holding member 130.

Modification of Sixth Embodiment

A modification of the sixth embodiment will now be described with reference to FIG. 22A to FIG. 22C. Here, a difference from the sixth embodiment will be explained, and like reference numbers denote like parts to omit a description thereof. As schematically shown in FIG. 22A, protruding portions 629 each having a coil-like shape in this modification are first accommodated in a first holding member 120. Likewise, protruding portions 639 each having a coil-like shape are first accommodated in a second holding member 130.

In this example, living tissue 900 is grasped by the first holding member 120 and the second holding member 130, then the protruding portions 629 and the protruding portions 639 protrude as shown in FIG. 22B, and holes are formed in the living tissue 900. Thereafter, the protruding portions 629 and the protruding portions 639 are again accommodated in the first holding member 120 and the second holding member 130. Subsequently, a high-frequency voltage is applied to the living tissue 900, and this tissue is heated. As a result, the living tissue 900 is welded. At this time, artificial collagen sheets 193 are dissolved by heat, and the dissolved collagen flows into the holes formed by the protruding portions 629 and the protruding portions 639. As a result, as shown in FIG. 22C, the collagen that has penetrated forms anchors 194, and strong welding is realized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical device which is configured to apply energy to living tissue and to be used to perform a surgical procedure, the device comprising:
    a grasping portion which is configured to grasp the living tissue having a first surface and a second surface facing the first surface;
    an incising portion which is movable forward and backward with respect to the living tissue grasped by the grasping portion and is configured to incise the living tissue;
    an introduction portion which is movable forward and backward with respect to the living tissue and is configured to introduce a biocompatible material, which is chemically bound with the living tissue by application of high-frequency energy, to a space between the first surface and the second surface of the incised living tissue; and
    a treatment portion which is configured to apply the high-frequency energy to the living tissue to chemically bind the biocompatible material with the living tissue, is also configured to apply thermal energy to the living tissue to weld the first surface and the second surface, and is provided on the grasping portion.

2. The device according to claim 1,
wherein the introduction portion includes a cover member which is configured to accommodate the biocompatible material therein, to be inserted into the space between the first surface and the second surface, to discharge the biocompatible material between the first surface and the second surface, and to be removed from the living tissue.

3. The device according to claim 1,
wherein the introduction portion is configured to:
    hold a casing which contains the biocompatible material, has strength enabling a puncture into the living tissue, and is taken into the living tissue or taken out from the living tissue;
    allow the casing to penetrate the inside of the living tissue from the outside of the living tissue, and insert the casing into the space between the first surface and the second surface; and
    place the casing between the first surface and the second surface.

4. The device according to claim 1,
wherein the biocompatible material is in a powdered form, and
the introduction portion includes a discharge portion which is configured to be inserted into the space between the first surface and the second surface, to discharge the powdered biocompatible material, and to be removed from the living tissue.

5. The device according to claim 1,
wherein the treatment portion includes a suction hole from which the living tissue is suctioned and which allows the living tissue to be adsorbed onto the surface of the treatment portion.

6. The device according to claim 1,
wherein the treatment portion includes a needle which is configured to penetrate the living tissue and allow the living tissue to adhere to the surface of the treatment portion.

7. The device according to claim 1, further comprising a tube through which air is supplied into the living tissue.

8. The device according to claim 1, further comprising a control apparatus which controls application of the high-frequency energy and application of the thermal energy using a heater.

9. An energized surgical method comprising:
    grasping living tissue having a first surface and a second surface facing the first surface by using a treatment portion;
    introducing a biocompatible material, which chemically binds with the living tissue, into a space between the first surface and the second surface;
    applying high-frequency energy to a portion where the first surface and the second surface of the living tissue face each other by using an electrode to weld the first surface and the second surface; and
    applying thermal energy to the portion where the first surface and the second surface of the living tissue face each other to weld the first surface and the second surface.

10. The method according to claim 9,
wherein applying the high-frequency energy is application that enables the biocompatible material and the first surface to be chemically bound with each other and enables the biocompatible material and the second surface to be chemically bound with each other, and
applying the thermal energy is application that enables welding the first surface and the second surface.

* * * * *